US012805896B2

(12) United States Patent
Fugerer et al.

(10) Patent No.: US 12,805,896 B2
(45) Date of Patent: Nov. 24, 2026

(54) SURGICAL CUTTING BLADE AND CONTROL FOR MULTI-APPLICATION PROCEDURES

(71) Applicant: Arthrex, Inc., Naples, FL (US)

(72) Inventors: Robert Fugerer, Lutz, FL (US); Brett Poole, St. Pete Beach, FL (US); Joshua Buckman, Naples, FL (US); Randall Hacker, Naples, FL (US)

(73) Assignee: Arthrex, Inc., Naples, FL (US)

( * ) Notice: Subject to any disclaimer, the term of this patent is extended or adjusted under 35 U.S.C. 154(b) by 0 days.

(21) Appl. No.: 18/924,172

(22) Filed: Oct. 23, 2024

(65) Prior Publication Data

US 2025/0134544 A1 May 1, 2025

Related U.S. Application Data

(60) Provisional application No. 63/545,974, filed on Oct. 27, 2023.

(51) Int. Cl.
*A61B 17/32* (2006.01)
*A61B 17/00* (2006.01)

(52) U.S. Cl.
CPC .................. *A61B 17/32002* (2013.01); *A61B 2017/00017* (2013.01); *A61B 2017/00398* (2013.01); *A61B 2017/320032* (2013.01); *A61B 2217/005* (2013.01)

(58) Field of Classification Search
CPC .............. A61B 17/32; A61B 17/32002; A61B 2017/00017; A61B 2017/00398; A61B 2017/320032; A61B 2217/005
USPC ..................................................... 606/79–85
See application file for complete search history.

(56) References Cited

U.S. PATENT DOCUMENTS 5,330,479 A * 7/1994 Whitmore .......... A61B 17/1604 606/79
5,733,298 A * 3/1998 Berman .................. H01H 3/14 606/167
5,766,199 A 6/1998 Heisler et al.
5,959,557 A 9/1999 Lim
8,226,677 B2 7/2012 Kauker et al.
8,414,606 B2 4/2013 Shadeck et al.
8,435,259 B2 5/2013 Dierck
8,568,418 B2 10/2013 Matusaitis et al.
8,574,254 B2 11/2013 Hedstrom et al.
9,358,036 B2 6/2016 Flynn et al.
9,655,640 B2 5/2017 Hedstrom et al.
9,839,441 B2 12/2017 Hayes et al.
(Continued)

*Primary Examiner* — Jessica Weiss
(74) *Attorney, Agent, or Firm* — Price Heneveld LLP

(57) ABSTRACT

A rotary surgical shaver includes an outer housing forming an outer cutting window at a distal end portion. A rotary member extends through the outer housing and in connection with a motor at a proximal end portion and forms a plurality of cutting windows comprising a first window and a second window at the distal end portion. A controller is configured to control the motor to position the rotary member over a first angular range aligned with the first window defining a first cutting sequence and control the motor to position the rotary member over a second angular range aligned with the second window defining a second cutting sequence. The controller is further configured to selectively adjust a duty cycle between the first cutting sequence and the second cutting sequence.

20 Claims, 14 Drawing Sheets

(56) References Cited

U.S. PATENT DOCUMENTS

| | | | | |
|---|---|---|---|---|
| 11,000,305 | B2 | 5/2021 | Smith et al. | |
| 2005/0065538 | A1 * | 3/2005 | Van Wyk | A61B 17/32002 606/159 |
| 2006/0212060 | A1 * | 9/2006 | Hacker | A61B 17/320016 606/180 |
| 2007/0282361 | A1 | 12/2007 | Da Rold et al. | |
| 2008/0208194 | A1 | 8/2008 | Bickenbach | |
| 2012/0310243 | A1 * | 12/2012 | Stratton | A61F 2/4644 606/79 |
| 2014/0100567 | A1 * | 4/2014 | Edwards | A61B 17/32002 606/45 |
| 2014/0277040 | A1 * | 9/2014 | Hayes | A61B 17/32002 606/170 |
| 2016/0346037 | A1 | 12/2016 | Truckai et al. | |
| 2021/0353321 | A1 * | 11/2021 | Jezierski | A61B 17/32002 |
| 2022/0167996 | A1 * | 6/2022 | Luedi | A61B 17/1624 |
| 2022/0249112 | A1 | 8/2022 | Magno et al. | |
| 2022/0378440 | A1 | 12/2022 | Fugerer et al. | |
| 2022/0378457 | A1 * | 12/2022 | Fugerer | G16H 40/63 |
| 2023/0200832 | A1 | 6/2023 | Germain | |

* cited by examiner

SURGICAL CUTTING BLADE AND CONTROL FOR MULTI-APPLICATION PROCEDURES

CROSS-REFERENCE TO RELATED APPLICATIONS

This application claims priority under 35 U.S.C. § 119(e) and the benefit of U.S. Provisional Application No. 63/545,974 entitled SURGICAL CUTTING BLADE AND CONTROL FOR MULTI-APPLICATION PROCEDURES, filed on Oct. 27, 2023, by Robert Fugerer, et al., the entire disclosure of which is incorporated herein by reference.

BACKGROUND

The present disclosure generally relates to an apparatus and a control method for a medical cutting device and, more particularly, relates to systems and methods for implementing an arthroscopic cutting device to improve operations at various stages of surgical procedures. In general, arthroscopic procedures are implemented to improve patient outcomes by limiting tissue damage through minimally invasive techniques. However, the blind nature of various procedures requires adept usage of surgical implements and tools that vary widely among procedures and the corresponding diverse surgical implements and apparatuses. In various implementations, the disclosure may provide for medical cutting devices that may be controlled to customize or modify the operation of various rotary cutting tools to suit the preferences of surgeons as well as improve the operation of the corresponding surgical implements in a variety of applications.

SUMMARY

The disclosure generally provides for a surgical cutting apparatus, control system, and corresponding methods of operation that may be used in arthroscopic surgeries to accomplish various procedures. In various implementations, the control methods and corresponding features provided by the apparatuses and systems disclosed may limit the need to exchange cutting blades or tools during various stages of a procedure. In this way, the disclosure may provide for improved performance and control in the operation of surgical cutting tools while limiting the time typically associated with removing, reconfiguring, and reinserting the cutting tool between procedural steps or stages. Accordingly, the disclosure may provide for improved operation and flexibility of medical cutting devices, particularly, arthroscopic cutting devices having rotating blades.

In various implementations, the disclosure may provide for a cutting device in the form of a rotary cutting blade that may comprise one or more cutting windows that rotationally engage an opening formed through a distal end portion. As later discussed in various examples, the cutting windows of the rotary cutting blade may be positioned about a perimeter wall formed by a rotary member and controlled to rotate over specific angular ranges within an elongated outer housing. By controlling and tracking the angular orientation of the rotary member, the associated control system may selectively activate the rotary cutting member to activate and engage a first cutting procedure associated with a first cutting window and/or a second cutting procedure associated with a second cutting window. Additionally, in various implementations, the control methods and devices described herein may provide for the activation of a plurality of combined cycles that may control the rotating member to selectively apply the first cutting procedure and the second cutting procedure over adjustable duty cycles. As further described in the exemplary implementations that follow, adjusting the duty cycle or percentages of operation over which different angular portions of the rotary cutting member is applied may provide for improved operation and customization to adjust an aggressiveness of cut and surface texture of tissue engaged by the rotary surgical apparatus disclosed.

In some implementations, the disclosure may further provide for a method of controlling an arthroscopic surgical tool. The method may comprise activating a plurality of cycles including a first oscillating rotation of a rotary member over a first angular range and a second oscillating rotation of the rotary member over a second angular range. The plurality of cycles including the first and second oscillation ranges may be controlled by applying each of the oscillating ranges in a predetermined sequence in rapid succession at a desired activation ratio. For example, the activation ratio may be adjusted, such that a first plurality of cycles of the first oscillating rotation over the first angular range is applied to more or fewer successive cycles than the second oscillating rotation over the second angular range. The sequential activation of the first and second oscillating rotations may be referred to as a duty cycle or an activation percentage of the total cycles of the first oscillating rotation and the second oscillating rotation. In this way, the method may control the operation of the surgical tool to suit a desired or procedurally required cutting style by adjusting the activation percentages of the first oscillating rotation and the second oscillating rotation.

In various implementations, the activation ratio of the first angular range may be adjusted to control 20% to 80% of the combined cycles as the first oscillating rotation over the first angular range. Alternatively, the activation ratio may be adjusted to control 20% to 80% of the combined cycles as the second oscillating rotation over the second angular range. In each case, a remaining portion of the combined cycles of the activation ratio may be applied to control the rotation of the rotary member over an opposite or alternate oscillating rotation or angular range. For example, if 80% of the combined cycles are controlled over the first oscillating rotation, the remaining 20% may be controlled over the second oscillating rotation and vice versa. In some implementations, one or more of the combined cycles may be applied over a third oscillating rotation, which may extend over a third angular range of rotation of the rotary member. By varying the activation ratio and corresponding duty cycles associated with the different oscillating rotations as described herein, the disclosure may provide for improved flexibility and control in the operation of the corresponding surgical implements.

These and other features, objects and advantages of the present disclosure will become apparent upon reading the following description thereof together with reference to the accompanying drawings.

DETAILED DESCRIPTION

In the following description, reference is made to the accompanying drawings, which show specific implementations that may be practiced. Wherever possible, the same reference numbers will be used throughout the drawings to refer to the same or like parts. It is to be understood that other implementations may be utilized and structural and functional changes may be made without departing from the scope of this disclosure.

Figure 1:
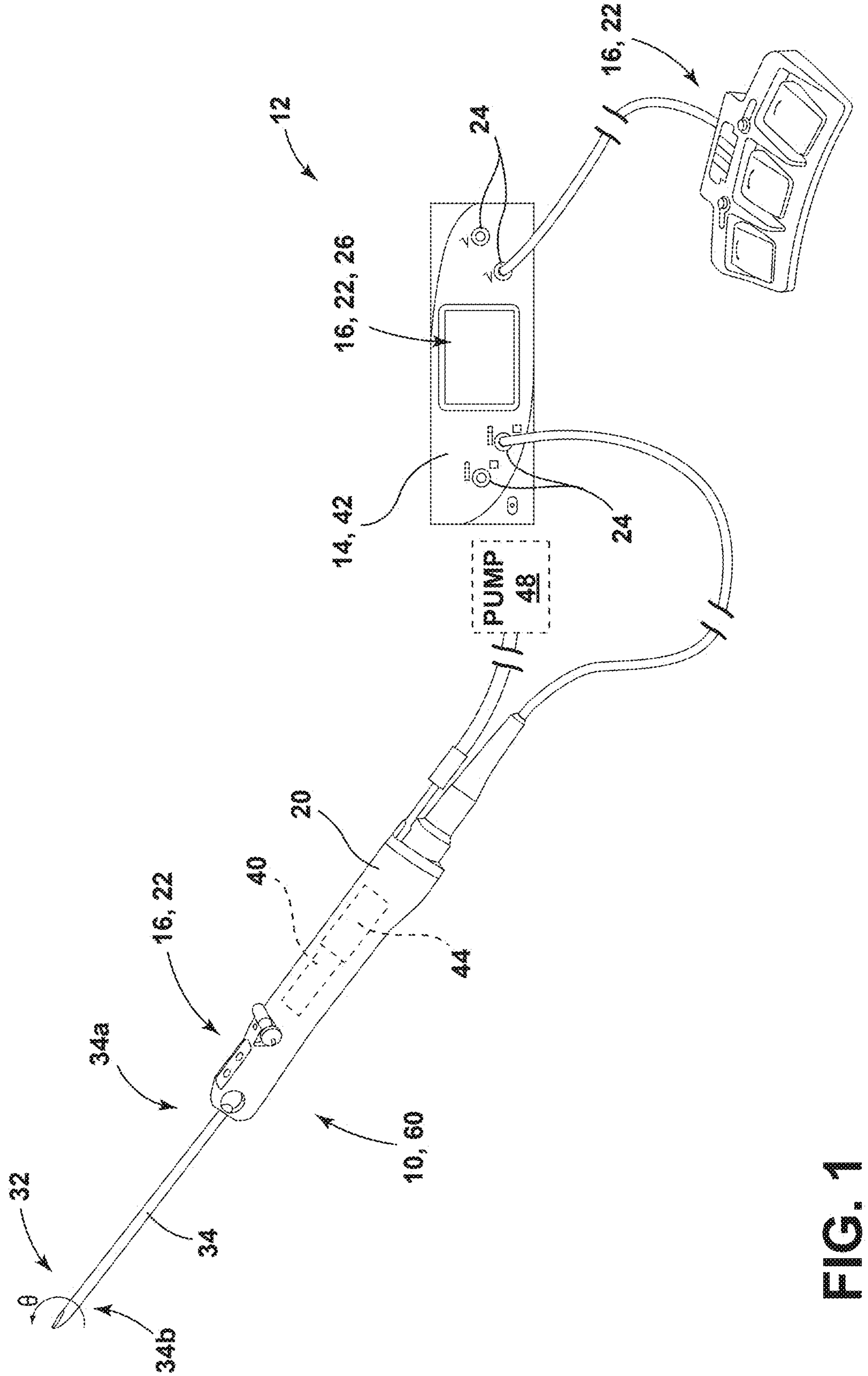
FIG. 1 is diagram demonstrating a handpiece comprising a surgical cutting device and corresponding control system.

Referring generally to FIGS. 1 and 2, the disclosure provides for a variety of features and operating methods related to the operation of a rotary surgical or cutting apparatus 10. As demonstrated, the surgical apparatus 10 may be implemented as a surgical tool or cutting accessory in communication with a surgical control system 12. In addition to the cutting apparatus 10, the control system 12 may include a control console 14 configured to receive control inputs from at least one user interface 16 that may be coupled to a handpiece 20 of the cutting apparatus 10 and/or one or more input accessories 22 (e.g., foot pedals, remote computers, interface devices, etc.). The input accessories 22 may be in communication with the control console 14 via one or more communication ports 24. In various implementations, the control console 14 may include a display screen 26 which may correspond to a touchscreen providing for an additional user interface 16 associated with the system 12. Accordingly, the surgical control system 12 may be selectively configured to control the operation of the cutting apparatus 10 as well as various related surgical tools.

In general, the cutting apparatus 10 may correspond to a variety of different forms of rotary cutting tools having one or more rotary cutting members 30 (e.g., blades, cutting windows, burrs, etc.) that may form a cutting head 32 of the apparatus 10. As shown, the cutting head 32 may be disposed at a distal end portion 34*b* of an elongated probe 34 extending from a proximal end portion 34*a* in connection with the handpiece 20. In this configuration, the cutting head 32 may be formed by at least one cutting window 40 as further discussed in reference to FIGS. 2A and 2B. As described throughout the disclosure, the rotation or oscillation of the cutting window 40 may be adjusted by a user via the user interface 16 to selectively implement various cutting routines or sequences to provide a desired cutting operation.

In various implementations as further discussed in reference to FIG. 10, the control console 14 may incorporate a controller 42 and/or control circuitry configured to control a rotational position θ of the one or more rotary cutting members 30 and further implement a variety of rotational cutting routines that may control a series or sequence of oscillations of the rotary cutting members 30. To effectuate the cutting operations or sequences of cutting routines, the controller 42 may communicate with a motor drive circuit 44 of the apparatus 10 that may be configured to control a motor 46 to selectively position the one or more rotary cutting members 30 to specified rotational positions θ in rapid succession. In such cases, a cutting routine may be adjusted to rotate the one or more cutting members 30 over rotational ranges of the rotational position θ, which may control a duty cycle between different cutting styles or levels of refinement or aggressiveness of cut to control the operation of the rotary surgical apparatus 10. In some cases, the motor drive circuit 44 and motor 46 may operate in concert to control the rotational position θ to increments of 5°, 3°, 1°, or even higher levels of precision depending on the specific use case and application for the cutting apparatus 10. In this way, cutting routines and operations supported by the cutting apparatus 10 and the control system 12 may provide for improved operation to implement a variety of control routines, some of which are described in the following detailed description.

Figure 2A:
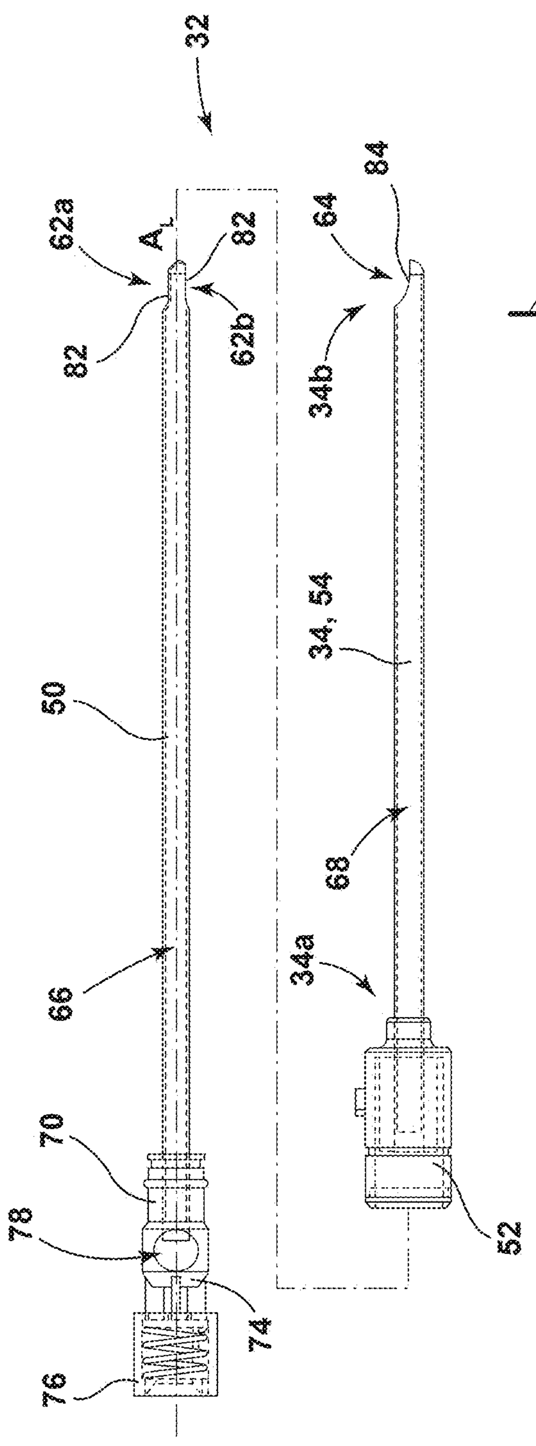
FIG. 2A is an exploded assembly view of a rotary cutting tool in the form of a shaver.
Figure 2B:
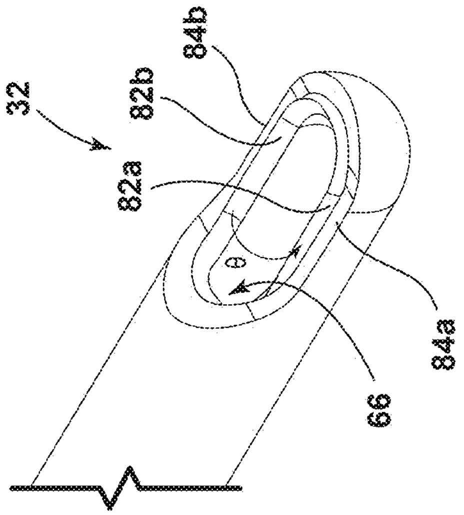
FIG. 2B is a projected assembly view of the rotary cutting tool demonstrating a cutting window and housing.

As further demonstrated in FIGS. 1 and 2, the cutting apparatus 10 may be in connection with a surgical pump 48 or vacuum pump that may be configured to draw fluid and debris from the surgical site of a patient from distal end 34*b* and through the elongated probe 34 via an interior aspiration passage 66. In operation, debris and/or fluids in a patient cavity may be retrieved through the aspiration passage 66 and the retrieved fluids may be replaced with clear surgical fluids (e.g., saline). In various implementations, the surgical control system 12 may coordinate the operation of the control console 14 of the cutting apparatus 10 with the operation of the pump 48. For example, a suction rate or intensity of the pump 48 may be controlled in coordination with one or more operating sequences and corresponding duty cycles of the cutting windows 40. As discussed in further detail in reference to FIGS. 2A and 2B, the effective suction rate achieved by the pump 48 via the aspiration passage 66 may be dependent on the alignment of a cutting window 40 of an inner rotary member 50 with a corresponding cutting window of a hub of the cutting head 32. By accurately tracking the position and controlling the rotational position θ of the cutting head 32, the controller 42 of the control console 14 may coordinate the operation of the pump to increase a suction rate or intensity in response to an alignment and/or a proportional duration of an alignment of the cutting windows 40 of the inner rotary member 50 and the hub 52 during the operation (e.g., rotation, oscillation, idle periods, duty cycles, control sequences, etc.) of the rotary surgical apparatus 10. In this way, the system 12 may provide for improved precision and customization of the cutting performance of the cutting head 32 while also adjusting the suction of the pump 48 to operate in coordination with the operation of the cutting head 32.

Referring now to FIGS. 2A and 2B, an exploded assembly view of the elongated probe 34 is shown demonstrating an inner rotary member 50 configured to engage a hub 52 extending distally through a housing 54 or rotary cylinder of the rotary member 50. In the exemplary implementation demonstrated, the surgical apparatus 10 may correspond to an arthroscopic shaver 60 having at least one inner window 62 formed by the inner rotary member 50 that may be selectively rotationally aligned with an outer window 64 formed through the housing 54 to effectuate a cutting operation as the rotary cutting member 30. In this configuration, the distal end 34*b* of the elongated probe 34 may be inserted into a patient cavity to access and manipulate patient tissue by aligning the cutting windows 40 with a target region of a patient for treatment.

Each of the inner rotary member 50 and the housing 54 may correspond to elongated, hollow, cylindrical bodies having side walls that form an aspiration passage 66 and a rotary passage 68, respectively. As denoted in the assembly view, the rotary member 50 may engage the rotary passage 68 via a hub adapter 70 formed in the hub 52 in connection with the housing 54. At the proximal end portion 34*a*, a drive shaft 74 may be coupled to the rotary member 50, which may further engage a drive assembly (e.g., an electrical motor) of the handpiece 20 via a shaft coupling 76. In this configuration, the rotary member 50 may rotate freely within the hub 52 and the housing 54 about a longitudinal axis $A_L$ of the elongated probe 34. In this way, the adjustment of a rotation of the motor 46 disposed in the handpiece 20 may freely adjust the rotational position θ of the rotary member 50 to selectively align the cutting windows 40 to accommodate various surgical applications and cutting routines.

Referring again to FIGS. 2A and 2B, in operation, the alignment of the at least one inner window 62 with the outer window 64 may be adjusted by controlling the rotational position θ of the rotary member 50. With the inner window 62 aligned with the outer window 64, the interior aspiration passage 66 may provide an interior pathway for fluid and/or debris to be recovered from a surgical site as a result of suction or vacuum pressure applied within the handpiece 20 or the hub 52 via an aspiration outlet 78. In this configuration, debris and/or fluids in a patient cavity may be retrieved through the aspiration passage 66 and the retrieved fluids may be replaced with clear surgical fluids (e.g., saline) via the surgical pump 48. The alignment of the at least one inner window 62 with the outer window 64 is demonstrated in detail in the projected view shown in FIG. 2B. As additionally demonstrated, the inner window 62 may be formed in the distal end portion 34*b* and extend along the longitudinal axis $A_L$ between a pair of inner cutting edges 82 that may selectively engage a pair of outer cutting edges 84 forming the outer window 64. In this configuration, the rotation of the rotary member 50 and adjustment of the rotational position θ may result in the inner cutting edges 82 rotationally sweeping adjacent to the outer cutting edges 84 as the rotational position θ is changed, thereby cutting tissue extending into the window 62 via a rotary scissor engagement. As further discussed in various examples throughout the disclosure, the inner cutting edges 82 and outer cutting edges 84 may be implemented in a variety of configurations to suit specific procedures and/or user preferences.

Figure 3B:
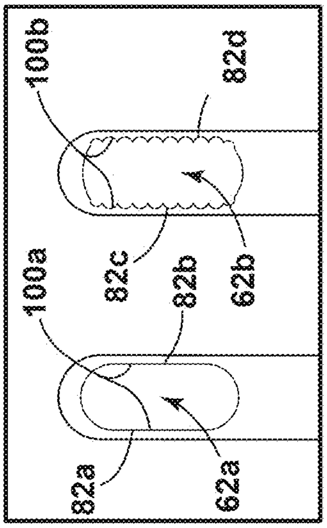
FIG. 3B demonstrates side profile views demonstrating exemplary edge configurations of the cutting windows of the cutting head demonstrated in FIG. 3A.
Figure 3C:
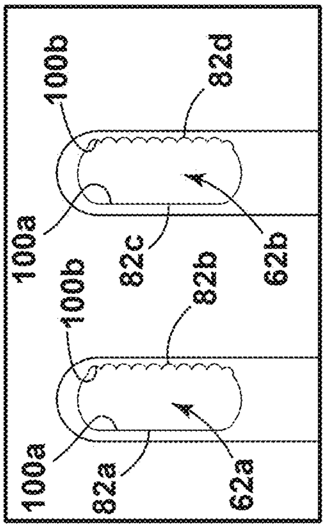
FIG. 3C demonstrates side profile views demonstrating exemplary edge configurations of the cutting windows of the cutting head demonstrated in FIG. 3A.
Figure 3A:
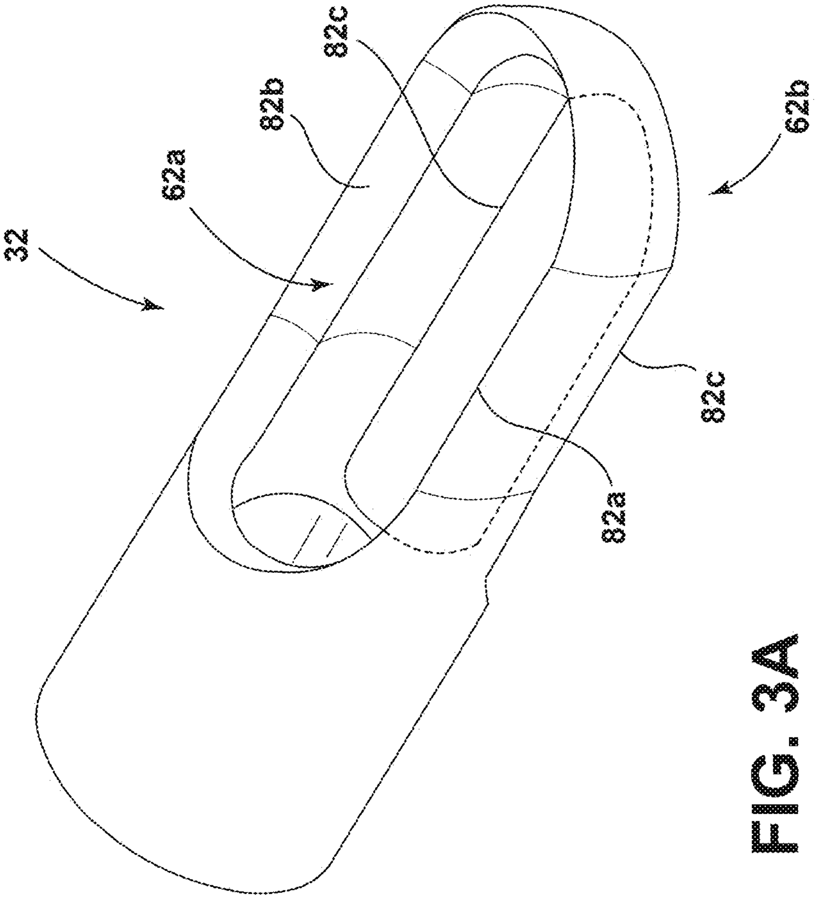
FIG. 3A is a detailed projected view of a distal end portion of a rotary member demonstrating a cutting head comprising a plurality of windows.

Referring now to FIG. 3A, the cutting head 32 of the rotary member 50 is demonstrated comprising a plurality of inner windows 62, including a first inner window 62*a* and a second inner window 62*b*. In the example shown, the inner windows 62 are formed on two opposing sides of the rotary member 50. Though two windows 62 are demonstrated in the example shown, additional windows 62 and corresponding cutting edges 82 may be implemented in a variety of ways, some of which are demonstrated in the examples shown in FIGS. 5 and 9. In operation, the controller 42 may control the motor drive circuit 44 to adjust the rotational position θ of the motor 46 to selectively align the first inner window 62*a*, the second inner window 62*b*, and/or additional inner windows 62*c*, 62*d* with the outer window 64. In general, the inner windows 62 may be rapidly oscillated to apply an alternating scissoring cut by the inner cutting edges 82 on opposing sides of each of the inner windows 62. Over time, a sequence of the oscillations may be adjusted between or among the inner windows 62 to effectuate a desired cutting operation.

As discussed in various detailed examples that follow, the controller 42 may control a sequence of oscillations over angular ranges Δθ. The angular ranges Δθ may correspond to changes in the rotational position θ that may cause the inner windows 62 to oscillate back and forth into and out of alignment with the outer window 64 in rapid succession as later demonstrated in FIGS. 7A and 7B. For example, the rotational position θ may be adjusted such that the first inner window 62*a* oscillates in successive clockwise and counterclockwise alignments with the outer window 64 over a first angular range Δθ1, such that the inner cutting edges 82 repeatedly engage the outer cutting edges 84. The oscillation and alignment of the first inner window 62*a* may be repeated over a specified count (e.g., number of oscillations) or percentage of an operating routine. Another portion of the operating routine may be implemented by the controller 42 controlling the rotational position θ, such that the second inner window 62*b* oscillates in successive clockwise and counterclockwise alignments with the outer window 64 over a second angular range 402. Similarly, the oscillation of the second inner window 62*b* may be repeated over a specified count (e.g., number of oscillations) or percentage of an operating routine that may form a cumulative oscillation count with the oscillation over the first inner window 62*a*. Accordingly, the controller 42 may control the routine to selectively apply each of the inner cutting windows 62 over a corresponding angular range 40 in a sequence, which may be adjusted to change a duty cycle or active period of each of cutting windows 62. In this way, the controller 42 may adjust a duty cycle of each of the cutting windows 62 and selectively apply a corresponding cutting style associated with a blade style 88 or an inner window size (e.g., window angle ω) of each of the cutting windows 62 to suit a desired cutting style or technique.

Referring now to FIGS. 3B and 3C, examples of cutting styles of the inner cutting edges 82 of the plurality of inner windows 62 are shown. Though discussed in reference to the inner cutting edges 82, it shall be understood that the outer cutting edges 84 may include similar style configurations. As shown, the inner cutting edges 82 may include a first inner edge 82*a*, a second inner edge 82*b*, a third inner edge 82*c*, and a fourth inner edge 82*d*. In the example shown in FIG. 3B, the first inner window 62*a* includes smooth cutting edges for the first and second cutting edge 82*a*, 82*b* and serrated edges for the third and fourth cutting edges 82*c*, 82*d*. Though discussed as smooth and serrated styles, it shall be understood that the styles may correspond to a wide variety of styles, some of which are demonstrated and discussed later in reference to FIG. 4. As shown in FIG. 3B, the opposing sides of each of the inner windows 62*a*, 62*b* include the same or similar blade styles. More specifically, the first inner window 62*a* includes inner edges 82*a*, 82*b*, both having smooth blade profiles. The second inner window 62*b* includes opposing cutting edges 82*c*, 82*d*, both having serrated blade profiles. In contrast, the inner windows 62 demonstrated in FIG. 3C include the inner edges 82 in a combined configuration having inner edges 82*a*, 82*d* with a smooth configuration and opposing inner edges 82*b*, 82*c* with a serrated or different blade configuration. Accordingly, each of the cutting edges 82, 84 may be implemented in various combinations to suit a desired application.

As shown in FIG. 3C, the combined blade style of the inner edges 82 may be arranged such that one of the opposing cutting edges (e.g., 82*a*, 82*c*) may be engaged based on a first directional rotation of the rotational position θ, in this case a clockwise direction. Similarly, the second inner edge 82*b* and fourth inner edge 82*d* may be selectively engaged by rotating the rotary member 50 in a second direction, in this case a counterclockwise direction. In this way, a style of blade or a combination of blade styles on the clockwise cutting edges 82*a*, 82*c* may differ from a blade style or combination of blade styles applied by the counterclockwise cutting edges 82*b*, 82*d*. In the examples demonstrated in FIG. 3B, the clockwise or counterclockwise operation would result in successive applications of a smooth inner edge 82*a*, 82*b* followed by a serrated inner edge 82*c*, 82*d*. Additionally, as shown in FIG. 3C, the clockwise operation of the cutting head 32 would result in successive applications of a smooth inner edges 82*a*, 82*c*, while the counterclockwise operation would result in successive applications of a serrated inner edges 82*b*, 82*d*. Accordingly, the cutting edges 82, 84 of the cutting head 32 may be implemented in a variety of ways to complement the operation of the rotary surgical apparatus 10.

Figure 4:
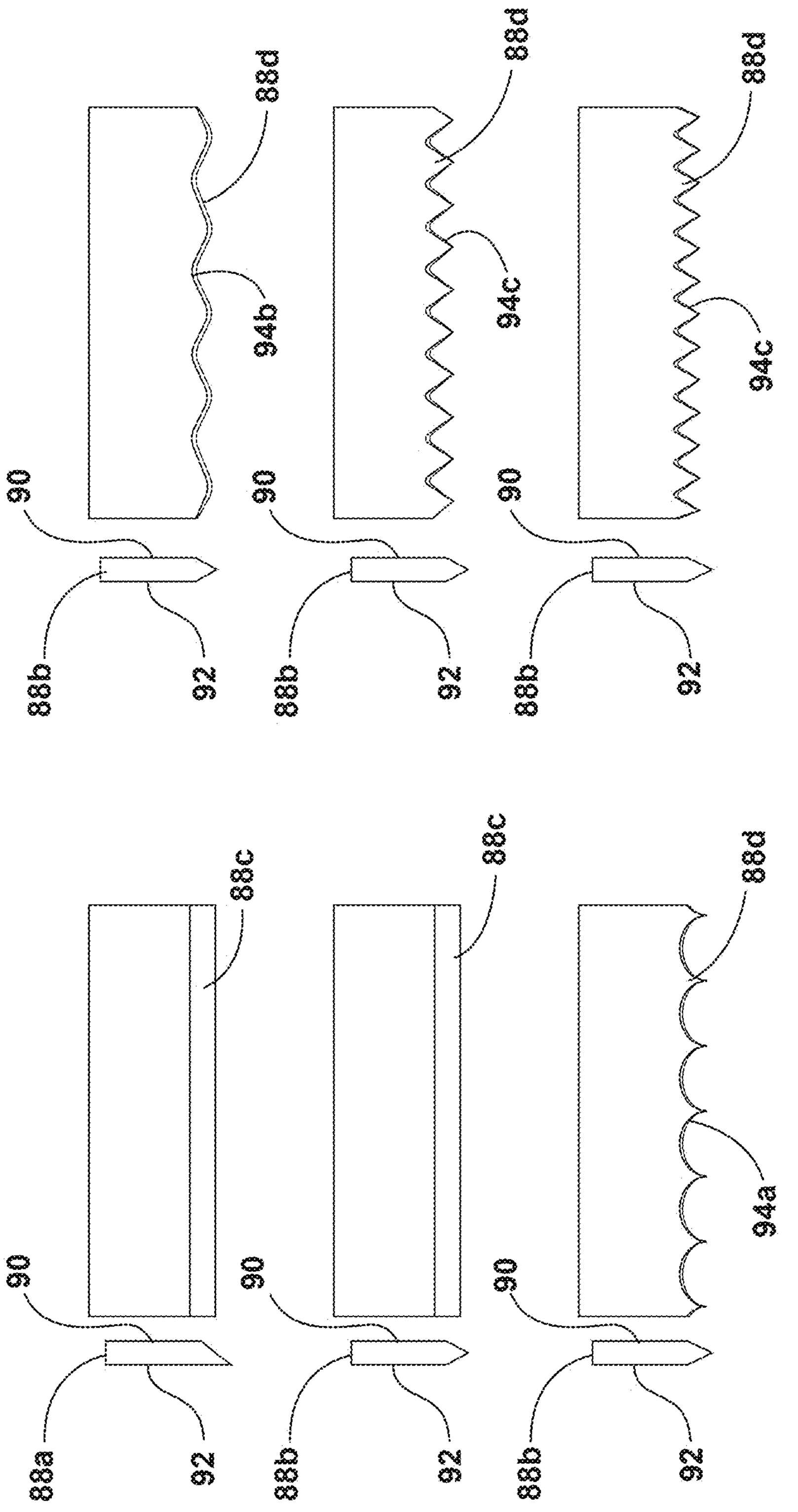
FIG. 4 demonstrates a variety of exemplary cutting profiles of the cutting edges formed by the cutting head and/or opening of the rotary surgical tool.

Referring now to FIG. 4, side profile views of a variety of blade styles 88*a*, 88*b*, etc. are shown which may be implemented in various combinations for the cutting edges 82, 84. As shown, the cutting edges 82, 84 may generally include a single bevel 88*a* where the blade tapers down a first side 90 or a double bevel 88*b* where the blade tapers down both the first side 90 and the second side 92. Additionally, each of the cutting edges 82, 84 may be implemented as smooth cutting edges 88*c* or serrated cutting edges 88*d*. Among the serrated edges 88*d*, a cutting profile 94 of the serrated edge may be implemented in a variety of profiles including, but not limited to, a scalloped edge 94*a*, a wavy edge 94*b*, and a sawtooth edge 94*c*. Depending on the desired cutting operation including a tissue removal rate and the resulting roughness of the exposed tissue surface, each of the blade styles 88 and cutting profiles 94 may be implemented in various combinations and applied in conjunction with the operating routines discussed herein to provide for improved operation of the cutting apparatus 10.

Referring now to FIGS. 5A-5D, several exemplary configurations of the inner edges 82 and the outer cutting edges 84 are shown demonstrating some of the various combinations of the blade styles 88 and configurations of the cutting windows 40. In general, each blade style 88 and cutting profile 94 of the cutting edges 82, 84 demonstrated in FIGS. 5, 6, 7, and 9 may be generally described as having a first blade style 100*a*, second blade style 100*b*, etc. to distinguish among multiple options. The blade styles 100*a*, 100*b*, etc. may used to distinguish among different blade styles 88 and cutting profiles 94 similar to those discussed in reference to FIG. 4. Accordingly, the terms first, second, third, etc., as discussed herein, may be used to distinguish among a variety of similar elements for clarity. The numeric designation (e.g., first, second, third, etc.) is not necessarily indicative of a number of different blade styles 100 or a required number of blade styles associated with any of the configurations discussed herein.

Figure 5A:
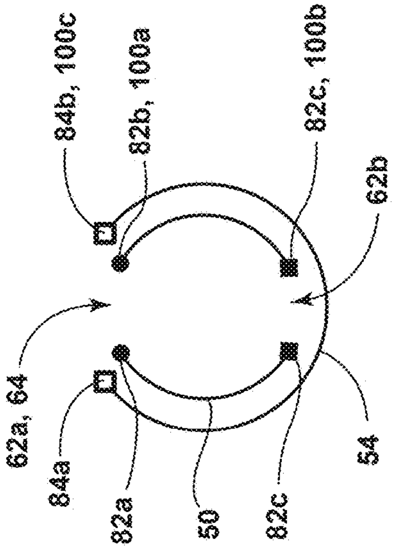
FIG. 5A is a simplified diagram demonstrating exemplary cutting edges of a rotary surgical apparatus.

As shown in FIG. 5A, a simplified depiction of the cutting head 32 is shown with the first and second inner edges 82*a*, 82*b* having a first style 100*a*. The third and fourth inner edges 82*c*, 82*d* may include a second blade style 100*b* that may differ from the first blade style 100*a*. Additionally, the first and second outer cutting edges 84*a*, 84*b* may comprise a third blade style 100*c*, which may differ from the first blade style 100*a* and/or the second blade style 100*b*. In this configuration, a controller 42 may control the motor 46 of the handpiece 20 to oscillate the first and second inner edges 82*a*, 82*b* over a first angular range Δθ1 relative to the first and second outer cutting edges 84*a*, 84*b* and, alternatively, control the third and fourth inner edges 82*c*, 82*d* to oscillate relative to the outer cutting edges 84*a*, 84*b* over a second angular range Δθ2. Further detailed examples of the oscillation and corresponding operation of the inner rotary member 50 are discussed in detail in reference to FIGS. 7A and 7B.

Figure 5B:
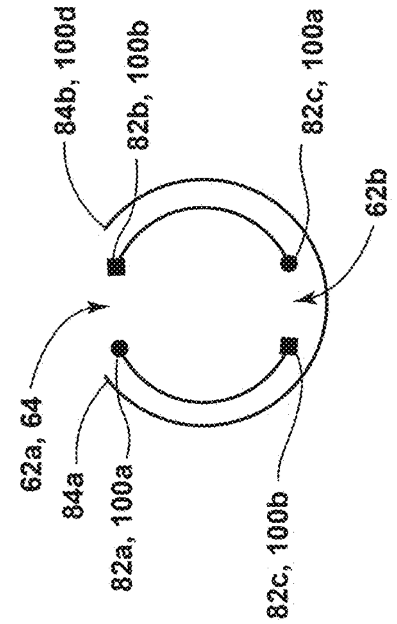
FIG. 5B is a simplified diagram demonstrating exemplary cutting edges of a rotary surgical apparatus.
Figure 5C:
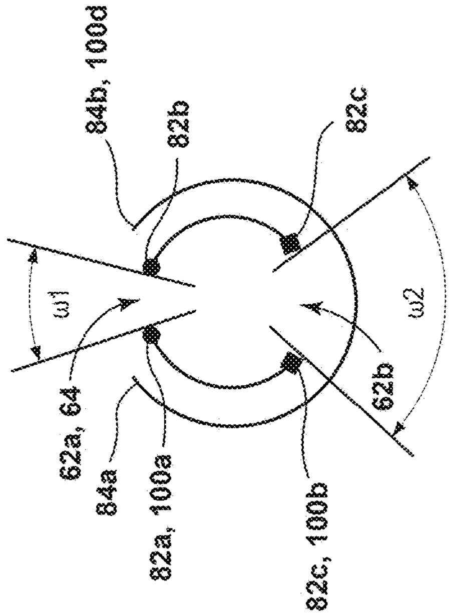
FIG. 5C is a simplified diagram demonstrating exemplary cutting edges of a rotary surgical apparatus.
Figure 5D:
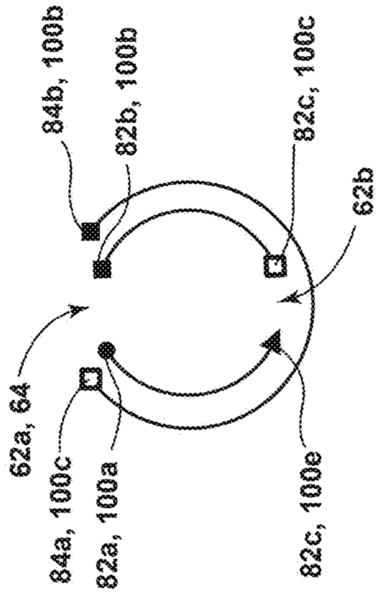
FIG. 5D is a simplified diagram demonstrating exemplary cutting edges of a rotary surgical apparatus.

FIGS. 5B-5D demonstrate additional configurations of the blade styles 100 of the cutting head 32 and may be described in reference to the distinguishing features relative to FIG. 5A for clarity. As shown in FIG. 5B, the first and second inner edges 82*a*, 82*b* may include a first blade style 100*a* and an opposing second blade style 100*b*, respectively. Similarly, the third and fourth cutting edges 82*c*, 82*d* may include the second blade style 100*b* and the first blade style 100*a* on opposing edges, respectively. The outer cutting edges 84*a*, 84*b* may include a fourth blade style 100*d* that may differ from one or more of the first, second, and third blade styles 100*a*-100*c*. Accordingly, each of the cutting edges 82, 84 may be combined in various arrangements.

Referring to FIG. 5C, the first inner window 62*a* may extend over a first window angle ω1 and the second inner window 62*b* may extend over a second window angle ω2. As shown, the window angles ω1, ω2 may define the proportions of the inner windows 62, which may effectively change the aspiration flowrate through the interior aspiration passage 66 and a cutting volume of the inner windows 62 based on the proportions denoted as the window angles ω1, ω2. As shown, the first and second window angles ω1, ω2 may extend over differing angular ranges. In the specific example provided, the first window angle ω1 is less than the second window angle ω2, forming a smaller inner window 62*a*. For example, the angular range of the first window angle ω1 may vary from approximately 20° to approximately 90° and a second angular range of the second window angle ω2 may vary from approximately 30° to 120°. As later discussed in reference to various operating routines, the oscillations of the inner rotary member 50 may be controlled over angular ranges 40 corresponding to the proportions of the inner windows 62 based on the window angles ω1, ω2. In this way, the adjustment of the duty cycles associated with each of the inner cutting windows 62 may be selectively adjusted to alternate between the different window angles ω1, ω2, etc. to vary a cutting intensity or cutting volume of tissue removed from the patient in response to each pass of the corresponding inner edges 82. For example, a larger window angle ω may result in a larger volume of tissue removed with each pass of the inner cutting edges 82. In this way, the control of the oscillation of the inner edges 82 relative to the outer cutting edges 84 may provide for variations in a volumetric cut rate of the patient tissue that may be applied alone or in combination with varying blade styles 100 as discussed herein.

Referring now to FIG. 5D, the first inner edge 82*a* may include a first blade style 100*a*, and the second inner edge 82*b* may include the second blade style 100*b*. Additionally, the fourth inner edge 82*d* may include the fourth blade style 100*d*, and the third inner edge 82*c* may include a fifth blade style 100*e*. As further demonstrated in FIG. 5D, the first outer cutting edge 84*a* may include the third blade style 100*c* and the second outer cutting edge 84*b* may include the second blade style 100*b*. Accordingly, the opposing blade faces of each of the inner cutting edges 82 and/or the outer cutting edge 84 may implement various blade styles 100 in matching or mismatched combinations, depending on a desired application of the cutting head 32.

Figure 6A:
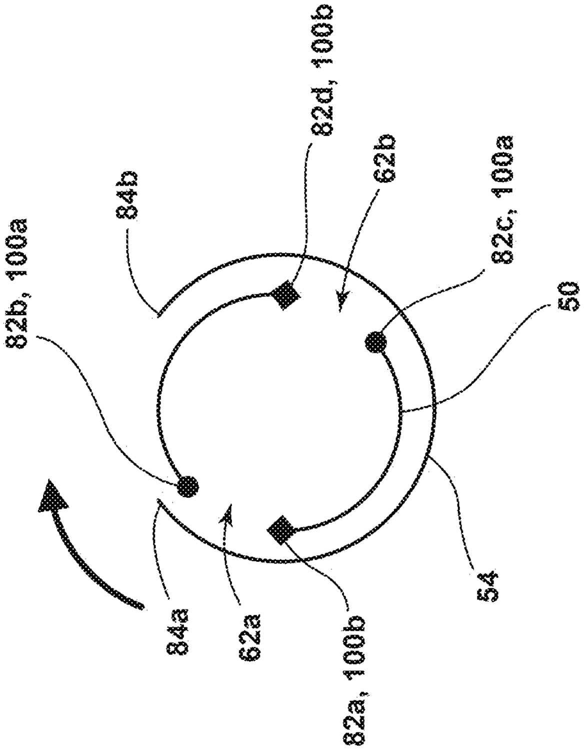
FIG. 6A is a simplified diagram of a cutting head demonstrating a clockwise operation.
Figure 6B:
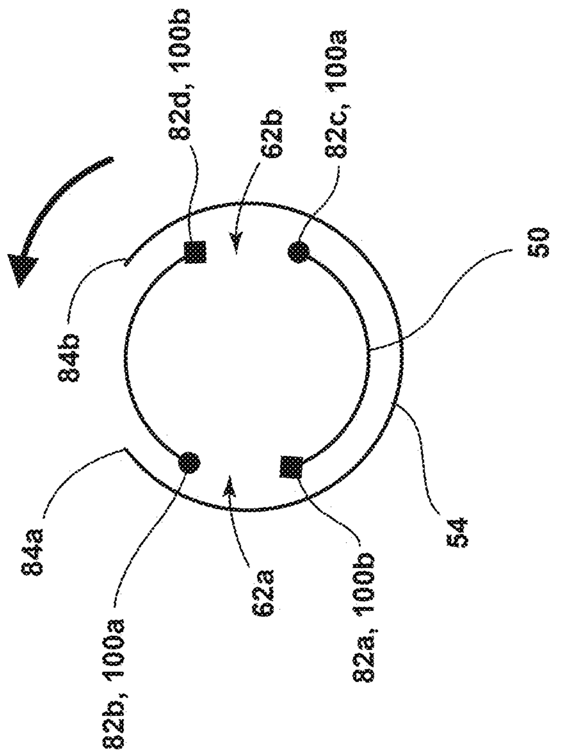
FIG. 6B is a simplified diagram of a cutting head demonstrating a counterclockwise operation.

Referring now to FIGS. 6A and 6B, an exemplary operation of the cutting head 32 is discussed in reference to a clockwise rotation 106 and a counterclockwise rotation 108. In the example shown, the inner cutting edges 82 of the inner rotary member 50 may include the second blade style 100*b* on the first inner edge 82*a* and the third inner edge 82*c*. Additionally, the first blade style 100*a* may be implemented on the second inner edge 82*b* and the fourth inner edge 82*d*. In this way, the clockwise rotation 106 of the inner rotary member 50 by the motor 46 may result in repeated engagement of the second blade style 100*b* of the first and third inner edges 82*a*, 82*c* with the outer cutting edges 84. Alternatively, the counter or anti-clockwise rotation 108 of the inner rotary member 50 may result in a repetitive engagement of the first blade style 100*a* of the second and fourth inner edges 82*b*, 82*d* to engage the outer cutting edges 84. In this configuration, the rotational control of the inner rotary member 50 may result in the engagement of a different blade style 100.

Figure 7A:
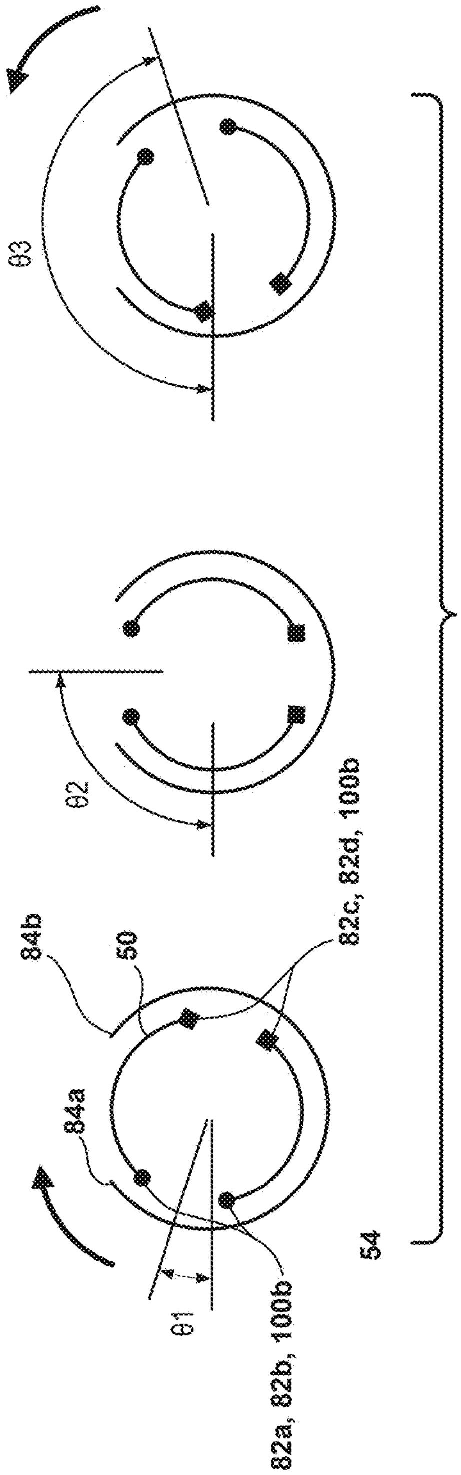
FIG. 7A demonstrates a sequence of angular orientations of a rotary member demonstrating a first angular range.
Figure 7B:
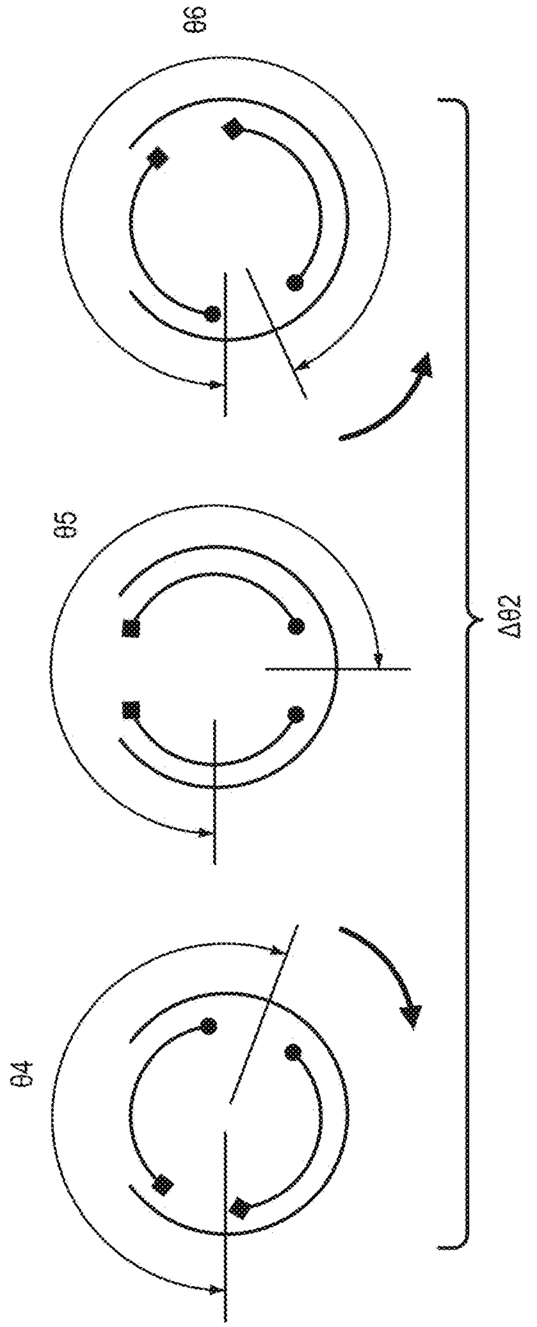
FIG. 7B demonstrates a sequence of angular orientations of a rotary member demonstrating a second angular range.

Referring now to FIGS. 7A and 7B, an exemplary operating routine of the rotary surgical apparatus 10 is shown demonstrating the oscillating operation of the cutting head 32 over a first angular range 401 and a second angular range Δθ2. As shown in FIG. 7A, the controller 42 may control the motor 46 to adjust the rotational position θ of the inner rotary member 50 from a first rotational position θ1 to a third rotational position θ3 via an intermediate second rotational position θ2. In this configuration, the first angular range Δθ1 may be defined between the first rotational position θ1 and the third rotational position θ3. As shown, the rotation of the inner rotary member 50 may cause the first blade style 100*a* of the first and second inner edges 82*a*, 82*b* to engage the outer cutting edges 84 of the outer window 64 over the first angular range Δθ1.

As shown in FIG. 7B, the controller may adjust the rotational position θ of the inner rotary member 50 over the second angular range 402. In operation, the controller 42 may adjust the rotational position from a fourth rotational position θ4 to a sixth rotational position θ6 via an intermediate fifth rotational position θ5. In this configuration, the second angular range 402 may be defined between the fourth rotational position θ4 and the sixth rotational position θ6. The rotation between the fourth rotational position θ4 and the sixth rotational position θ6 may cause the second blade style 100*b* of the third and fourth inner cutting edges 82*c*, 82*d* to engage the outer cutting edges 84 of the outer window 64. In various implementations, the controller 42 may control the motor drive circuit 44 to cause the inner rotary member 50 to oscillate over the first angular range Δθ1 and the second angular range 402 in rapid succession. Additionally, the controller 42 may adjust a duty cycle between the first angular range Δθ1 and the second angular range Δθ2 to engage the corresponding blade styles 100*a*, 100*b* and/or cutting window proportions (e.g., the window angles w) to adjust a cutting rate (e.g., tissue removal over time or per pass) and a smoothing or aggressiveness of the cutting head 32 by adjusting the duty cycle of the corresponding cutting window 62. In this way, the disclosure may provide for the selective utilization or application of each of the inner cutting edges 82*a*-82*d* in rapid succession to apply various cutting sequences and/or routines.

Figure 8:
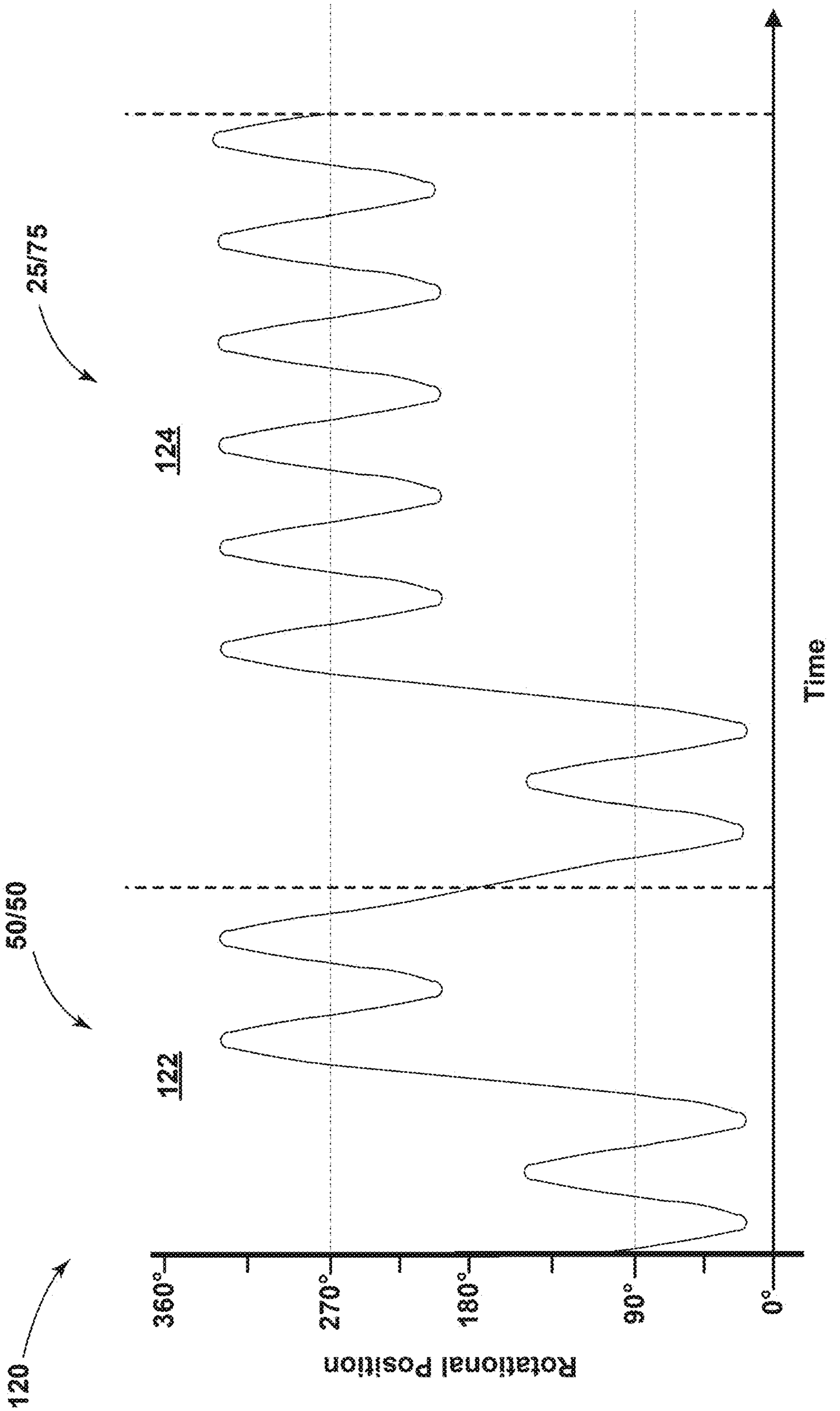
FIG. 8 is a plot demonstrating an adjustable duty cycle or activation ratio of a plurality of cutting procedures that may be adjustably implemented by a rotary surgical apparatus.

Referring now to FIG. 8, a plot 120 is shown demonstrating the rotational position θ of the inner rotary member 50 over time demonstrating a first duty cycle 122 applied over a first angular range 401 and a second duty cycle 124 applied over a second angular range Δθ2. In operation, the controller 42 may control the inner rotary member 50 to oscillate over the first angular range Δ01 and the second angular range Δθ2 in approximately equal parts or percentages. For example, the controller 42 may control the rotational position θ of the inner rotary member 50 to cycle the first and second inner edges 82*a*, 82*b* past the outer cutting edges 84 an equal number of times sequentially to the third and fourth inner edges 82*c*, 82*d*. In this configuration, the first and second inner edges 82*a*, 82*b* may be applied approximately 50% of the operating time and the third and fourth inner edges 82*c*, 82*d* may be applied approximately 50% of the operating time. Such operation may provide a balanced application of the blade styles 100, window angles w, or corresponding features of each of the inner windows 62 in approximately equal parts.

As shown in the example of the second duty cycle 124, the inner rotary member 50 may be controlled to oscillate over the first angular range 401 for approximately 25% of the oscillations compared to the second angular range 402 over approximately 75% of the oscillations. For example, in the exemplary sequence shown, the rotational position θ is controlled over the first angular range Δθ1 for approximately two cycles compared to approximately six cycles for the second angular range Δθ2. In this configuration, the first and second inner edges 82*a*, 82*b* may be applied 25% of the time while the third and fourth inner edges 82*c*, 82*d* may be applied approximately 75% of the time or for 75% of the total oscillations. Such operation may cause the blade style 100 of the first and second inner edges 82*a*, 82*b* to be applied less (e.g., three times less) than the blade style 100 of the third and fourth cutting edges 82*c*, 82*d*. Accordingly, in various implementations, the controller 42 may adjust the duty cycle or percentage of oscillations over multiple angular ranges 40 to adjust a corresponding cutting style (e.g., aggressiveness, smoothing, cutting volume, etc.) based on the duty cycle of each of the inner windows 62*a*, 62*b* of the inner rotary member 50. As described in the previous examples, a 50/50 duty cycle may provide for approximately equal application of the cutting edges 82 of the first inner window 62*a* and the second inner window 62*b*. A 25/75 duty cycle may apply the cutting edges 82 of the first inner window 62*a* three time less than those of the second inner window 62*b*. In various implementations, the duty cycles of each of the inner windows 62 and associated angular ranges 40 may vary from approximately 5% to 95% for the application of each of the cutting edges 82 of the inner window 62, 62*b*, 62*c*, etc. Additionally, the sequence of operation of the inner rotary member 50 may include one or more period of oscillation over additional rotational ranges 40, repeated clockwise or counterclockwise rotations, and/or idle periods/aspiration periods, wherein a selected one of the inner windows 62 may be aligned with the outer window 64 to maximize aspiration. Accordingly, the operating routines and sequences of operation described herein may be implemented in a number of ways to improve the operation of the rotary surgical apparatus 10.

Though discussed generally as percentages or portions of a total number of oscillations of each of the angular ranges 40, the controller 42 may control the rotational position θ of the inner rotary member 50 in various control sequences. For example, the respective oscillations of the inner rotary member 50 over the first angular range 401 and the second angular range 402 may be controlled over a sequence including a defined number of oscillations over the first angular range Δθ1, a second defined number of oscillations over the second angular range 402, and/or one or more idle periods or rotations over a third angular range Δθ3. For example, the first defined number of oscillations of the first angular range Δθ1 may include one, five, twenty, or more consecutive oscillations. Similarly, the second defined oscillations of the second angular range 402 may include one, five, twenty, or more consecutive oscillations. The number of oscillations over each angular range 40 may be varied in any desired combination to suit the desired operation. In this way, the application of the specific angular ranges 40 of the inner cutting edges 82 may be selectively applied in various sequences to suit the preferences of users and improve operations to suit various surgical techniques.

As previously discussed, the system 12 may be controlled such that the operation cutting head 32 (e.g., angular position θ, cutting or control sequence, duty cycles of cutting windows 62, etc.) is controlled in coordination with the suction of the pump 48. The effective suction rate achieved by the pump 48 via the aspiration passage 66 may be dependent on the alignment of a cutting window 40 of an inner rotary member 50 with a corresponding cutting window of a hub of the cutting head 32. Additionally, depending on the configuration of the cutting head 32 the window angle ω and corresponding proportions of the inner windows 62 may vary in size, which may change the effective suction rate of the pump 48. Accordingly, the system 12 may provide for improved operation of the pump 48 by controlling one of more suction or fluid flow settings based on the angular position θ of the inner rotary member 50 throughout the operation of the rotary surgical apparatus 10. In various cases, the suction settings or intensity of the pump 48 may similarly be controlled in response to a proportional duration of an alignment of the cutting windows 62, 64 during a control sequence, duty cycle, etc. of cutting windows 62, which may be determined based on the specific angular ranges Δθ of the inner cutting edges 82 over the corresponding operating time of the pump 48. By accurately tracking and controlling the rotational position θ of the cutting head with the controller 42, the system 10 may control and coordinate the operation of the pump 48 to improve or maintain the operating efficacy of the pump 48 when the cutting apparatus 10 is implemented.

For example, throughout each of the cutting sequences or routines, the controller 42 may control and track the rotational position θ of the cutting head 32. Based on the variations of the rotational position θ over time, a proportional duration of an alignment or alignment proportion of the cutting windows 62, 64 may vary. The alignment proportion may correspond to a percentage of an operating sequence or duty cycle of the cutting head 32 where one of the inner cutting windows 62 is aligned with the outer window 64. Based on the changes in the rotational position θ over time, the controller 42 may calculate an effective alignment proportion of the operation of the shaver 60 during which the windows 62, 64 are aligned. The effective alignment proportion may be dependent on the duration over which the windows 62, 64 are aligned or partially aligned throughout the angular operating range 40 of each operating sequence or duty cycle. In such cases, the controller 42 may adjust or increase the suction or control settings of the pump to proportionally adjust the suction from a baseline setting (e.g., wherein the windows 62, 64 are aligned) to an increase suction setting increased proportionally to the effective alignment proportion of the windows 62, 64 over the active operating sequence and corresponding angular operating ranges 40 of the rotary member 50.

In some cases, the effective suction of the pump 48 may also vary based on a rotation or oscillation speed of the cutting head 32. For example, when the rotation or oscillation speed increases, the effective suction of the pump 48 may change or decrease due to obstructions or debris that may not be collected into the interior aspiration passage 66 due to the increasingly limited duration of the alignment of the windows 62, 64 proportionate to the speed. Such interruptions to the suction and outflow from the patient operating site may similarly decrease the effective suction rate of the pump 48. Accordingly, the controller 42 of the system 12 may communicate with the pump 48 to adjust the outflow rate (e.g., the suction rate or intensity) in response to the increased oscillation or rotation speed similar to and in combination with the adjustments responsive to the proportional alignment of the windows 62, 64.

In some cases, the controller 42 of the cutting apparatus 10 may operate similarly in coordination with the pump 48 to improve the effective suction rate of the fluid and debris from the patient cavity. For example, in some cases, the controller 42 may control the operation of the motor 46 to align the windows 62, 64 upon stopping or pausing a cutting operation of the cutting head 32. Similarly, one or more aligned or partially aligned aspiration periods may be interleaved into an operating sequence to periodically align or increase an alignment of the inner windows 62 with the outer window 64 during a cutting operation. For Example, an alignment period may correspond to a complete alignment of the windows 62, 64 for a predetermined period interleaved into the cutting sequences. Similarly, the angular operating ranges 40 of one or more cutting sequences may be adjusted to increase the alignment proportion of the window 62, 64 by adjusting the sequence of the rotational position θ for one or more periodic cutting passes. For example, rather than cutting by controlling the inner cutting window 62 to pass the outer cutting window 64 in its entirety in each oscillating pass, during some passes, the inner window 62 may only partially pass the outer window 64, such that the window 62, 64 are aligned for an increased proportion of the operation of the cutting head 32. In operation, the changes in the angular operating ranges Δθ of one or more cutting sequences may be adjusted in combination with the preferred intensity or aggressiveness of the cutting apparatus 10, such that the effective suction of the pump 48 may be improved while also allowing the cutting apparatus to operate according to the procedural requirements and/or the user preferences.

As previously discussed, the window angle ω and corresponding proportions of the inner windows 62 may vary in size, which may also change the effective suction rate of the pump 48. The cause of the change in the effective suction rate of the pump 48 may be a change in the proportions of a cross-sectional flow path through aligned windows 62, 64 and into the interior aspiration passage 66 through which the fluid and debris pass to the pump 48. In order to account for such changes, the controller 42 may communicate with the pump 48, such that the suction settings (e.g., outflow rate, suction intensity, vacuum pressure, etc.) are updated proportional to the corresponding cross-sectional flow path through aligned windows 62, 64. For example, in cases where one of the inner windows 62 is smaller than the outer window 64, the alignment of a first inner window (e.g., the first window 62*a* in FIG. 5C) with the outer window 64 may limit a flow path into the interior aspiration passage 66 relative to the alignment of a second inner window (e.g., the second window 62*b* in FIG. 5C). Additional examples of variations in the window angle ω and the corresponding proportions of the inner windows 62 that may adjust or limit the effective suction of the pump 48 into the interior aspiration passage 66 are demonstrated in FIGS. 9A and 9B.

To effectuate the various operations of the cutting apparatus 10 and the coordinate operation of the pump 48, the controller 42, the arrangement of the inner window(s) 62, the outer window 64, the window angles w, and the rotational positions θ may be programmed into, accessed by, or otherwise identified by the controller 42 for each of the configurations of the cutting head 32. For example, the cutting style, features, and dimensions of the cutting windows 62, 64 may be identified in response to a manual programming input, selection via an accessory library or database, and/or detected by the controller 42 based on information accessed from the cutting head 32. In some cases, identifying style, model, dimensional, operating speed ranges and limits, usage restrictions (time limits, cutting pass limits, etc.), manufacturer information, usage statistics and various forms of information related to the cutting head 32 may be accessed by the controller 42. Such information may be accessed via an electronic identification circuit or tag (e.g., radio frequency identification [RFID]) incorporated in the cutting head 32 (e.g., the hub adapter 70). The electronic identification circuit may be accessed by the controller 42 by one or more communication circuits 156 or communication ports 24 as later discussed and demonstrated in reference to FIG. 14. In this way, the controller 42 may update the operation of the cutting apparatus 10 in response to the specific style, dimensions, and operating configurations of each of the interchangeable cutting heads 32 as discussed herein.

Figure 9B:
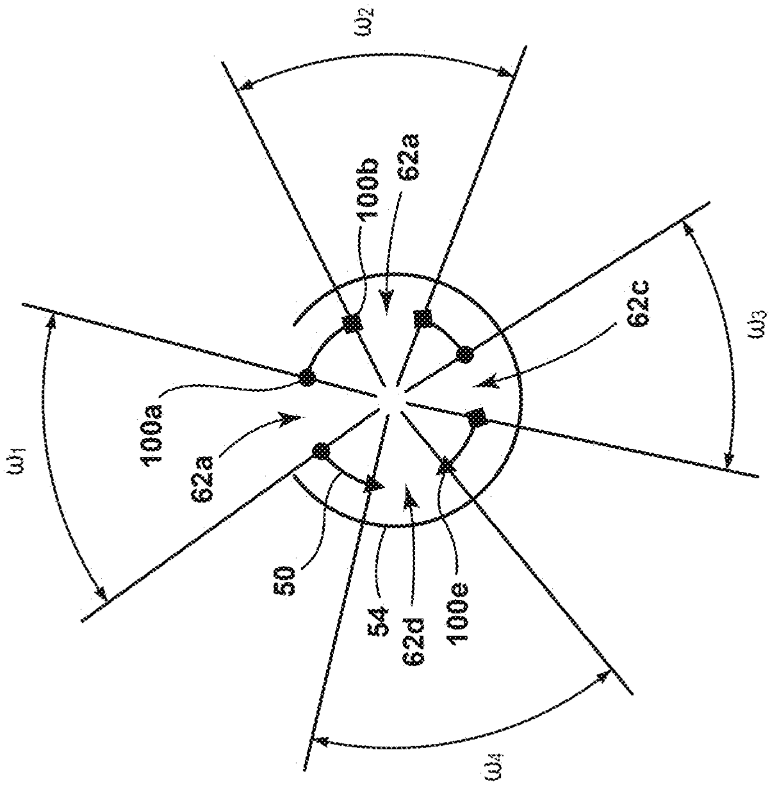
FIG. 9B is a simplified diagram demonstrating exemplary cutting edges of a rotary surgical apparatus.
Figure 9A:
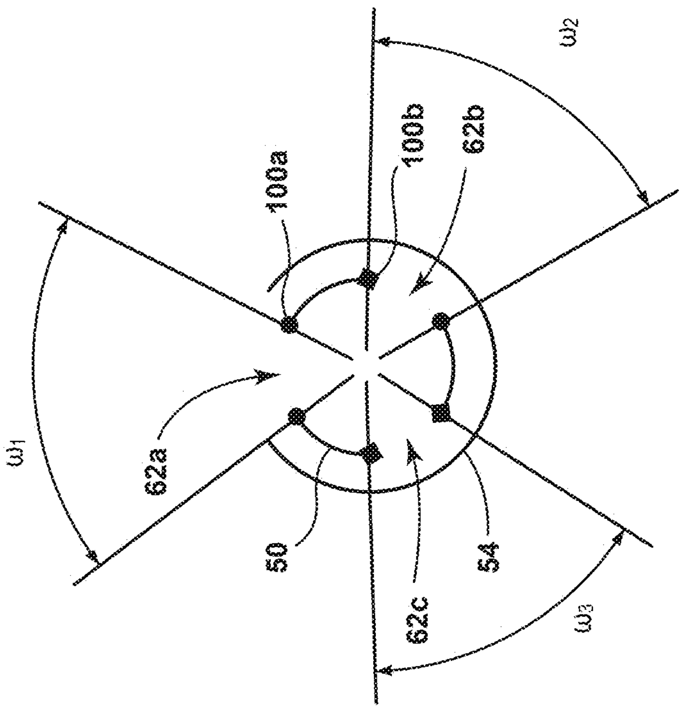
FIG. 9A is a simplified diagram demonstrating exemplary cutting edges of a rotary surgical apparatus.

Referring to FIGS. 9A and 9B, the cutting head 32 may be implemented to include additional inner windows 62 and corresponding inner cutting edges 82. As shown in FIG. 9A, the inner rotary member 50 includes the first inner window 62*a*, the second inner window 62*b*, and a third inner window 62*c*. As previously discussed, each of the inner windows 62 may form an opening through the side wall of the inner rotary member 50 extending over a corresponding window angle ω. As shown, the first inner window 62*a* extends over a first window angle ω1; the second inner window 62*b* extends over a second window angle ω2; and the third inner window 62*c* extends over a third window angle ω3. In this configuration, the controller 42 may adjust the rotational position θ of the inner rotary member 50 to selectively apply each of the cutting edges 82 formed along opposing sides of the inner windows 62 by oscillating the rotational position θ over angular range 40 corresponding to each of the window angles ω1, ω2, ω3. In the example of FIG. 9B, a fourth inner window 62*d* is formed through the inner rotary member 50. The fourth inner window 62*d* may form an opening extending through the inner rotary member 50 over a fourth window angle ω4. In such implementations, the controller 42 may adjust the rotational position θ to oscillate over the angular range Δθ corresponding to each of the window angles ω1, ω2, ω3, and/or ω4.

As previously discussed, each of the inner cutting edges 82 may include blade styles 100 that may differ on opposing sides or in each of the inner windows 62. Accordingly, the controller 42 may control the rotational position θ to apply each of the blade styles 100 corresponding to the inner cutting edges 82 of the inner windows 62 to selectively adjust the cutting style and operation of the rotary surgical apparatus 10. As provided by various exemplary routines and apparatuses, the rotary surgical apparatus 10 may support a wide variety of operations that may improve surgical procedures and allow the operation of the system 12 to be tailored or customized to suit various user preferences.

Figure 10A:
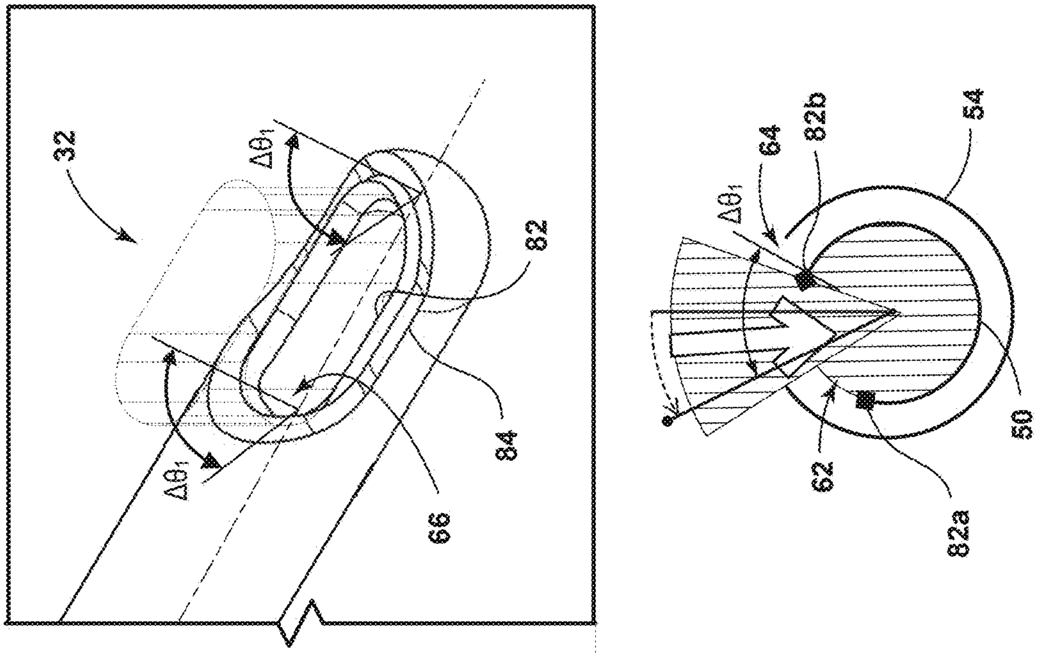
FIG. 10A is a projected assembly view of a rotary cutting tool demonstrating an alignment of a cutting window over a first rotational range.

Referring now to FIGS. 10A, 10B, 11, 12, and 13; the operation of the cutting apparatus 10 is further described in reference to several controlled procedures that may generally provide for a controlled alignment of the inner cutting window 62 and the outer window 64 to effectively maintain a flow passage 130 (e.g., a suction or aspiration passage) throughout a controlled rotary operation of the cutting head 32. Accordingly, the operation of the cutting apparatus 10 may prioritize the alignment of the windows 62, 64 throughout various cutting routines, similar to the duty cycles 122, 124 previously discussed. As demonstrated in FIG. 10A, the rotational position θ of the inner rotary member 50 may be controlled over a first angular range 401 that may be centered with the windows 62, 64 aligned, maximizing the corresponding flow passage 130. As shown in FIG. 10A, the rotational position θ is oriented on one of the angular extremities defining the first angular range Δθ1. In this position, a majority of the flow passage 130 is maintained while a portion of the second cutting edge 82*b* intersects and closes a portion of the flow passage 130. By operating over the first angular range 401 depicted in FIG. 10A, the opposing inner cutting edges 82 of the inner rotary member 50 may serve to agitate turbulent matter that may be passing through the flow passage 130 while maintaining the alignment of the windows 62, 64 over the majority of the flow passage 130. As described herein, the majority of the flow passage 130 may correspond to a portion of 50%, 60%, 70%, or larger proportions. Additionally, in some implementations, the alignment of the windows 62, 64 may be maintained over the angular range Δθ1 ensuring that at least a portion of the flow passage 130, for example, 10%, 20%, 30%, or more, is maintained by the alignment of the inner window 62 and the outer window 64 over the angular range Δθ1. In this way, the control procedure of the inner rotary member 50 may provide for maintaining a portion of the flow passage 130 over the first angular range Δθ1 to selectively maintain the flow therethrough.

Figure 10B:
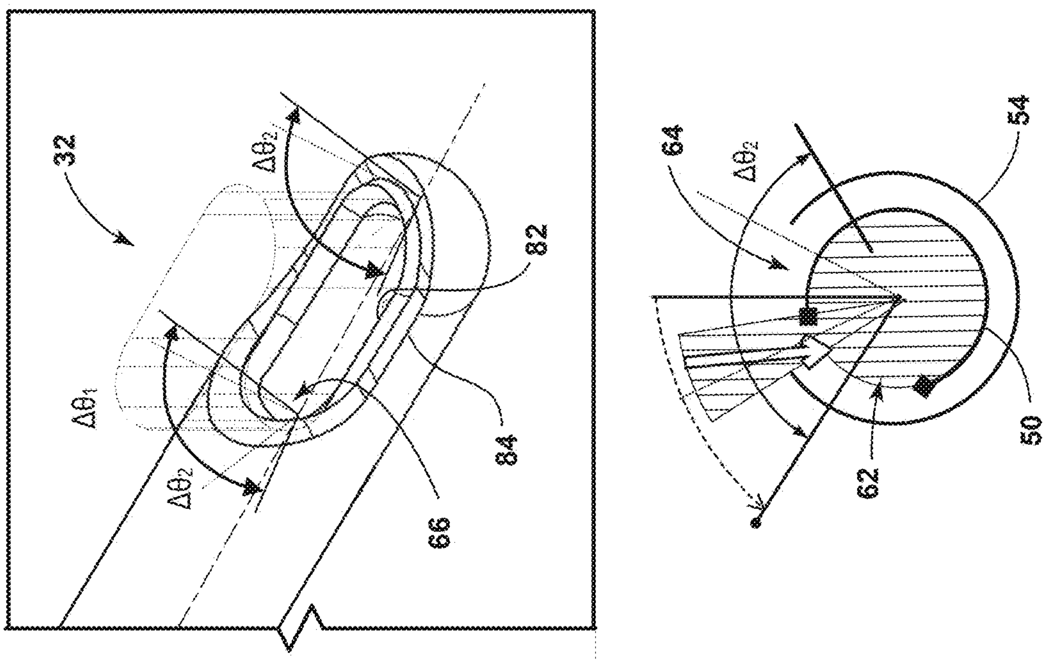
FIG. 10B is a projected assembly view of a rotary cutting tool demonstrating the alignment of a cutting window over a second rotational range.

As demonstrated in FIG. 10B, the rotational position Δθ of the inner rotary member 50 may similarly be controlled over a second angular range Δθ2. As shown, angular range Δθ2 may extend over a larger angular range than Δθ1 as previously described in reference to FIG. 10A. In the example shown, the second angular range 402 may similarly provide for the at least partial alignment of the windows 62, 64 to maintain a portion of the flow passage 130 over the corresponding range of rotational positions θ of the inner rotary member 50. By increasing the extent of the change in the rotational position θ over the second angular range 402, the operation of the cutting apparatus 10 may provide for increased cutting or tissue removal relative to the operation associated with the control over the first angular range Δθ1. In this way, the controller 42 of the control console 14 may selectively adjust between a cutting or biting operation associated with the second angular range 402 and a swallowing or agitation range associated with the first angular range 401. The controller 42 may adjust the operation of the cutting apparatus 10 to increase a tissue removal over a first duration associated with the second angular range 402 and, alternatively, prioritize maintaining the flow passage 130 over the second angular range Δθ1 to remove matter freed or released during operating cycles over the second angular range Δθ2.

Figure 11:
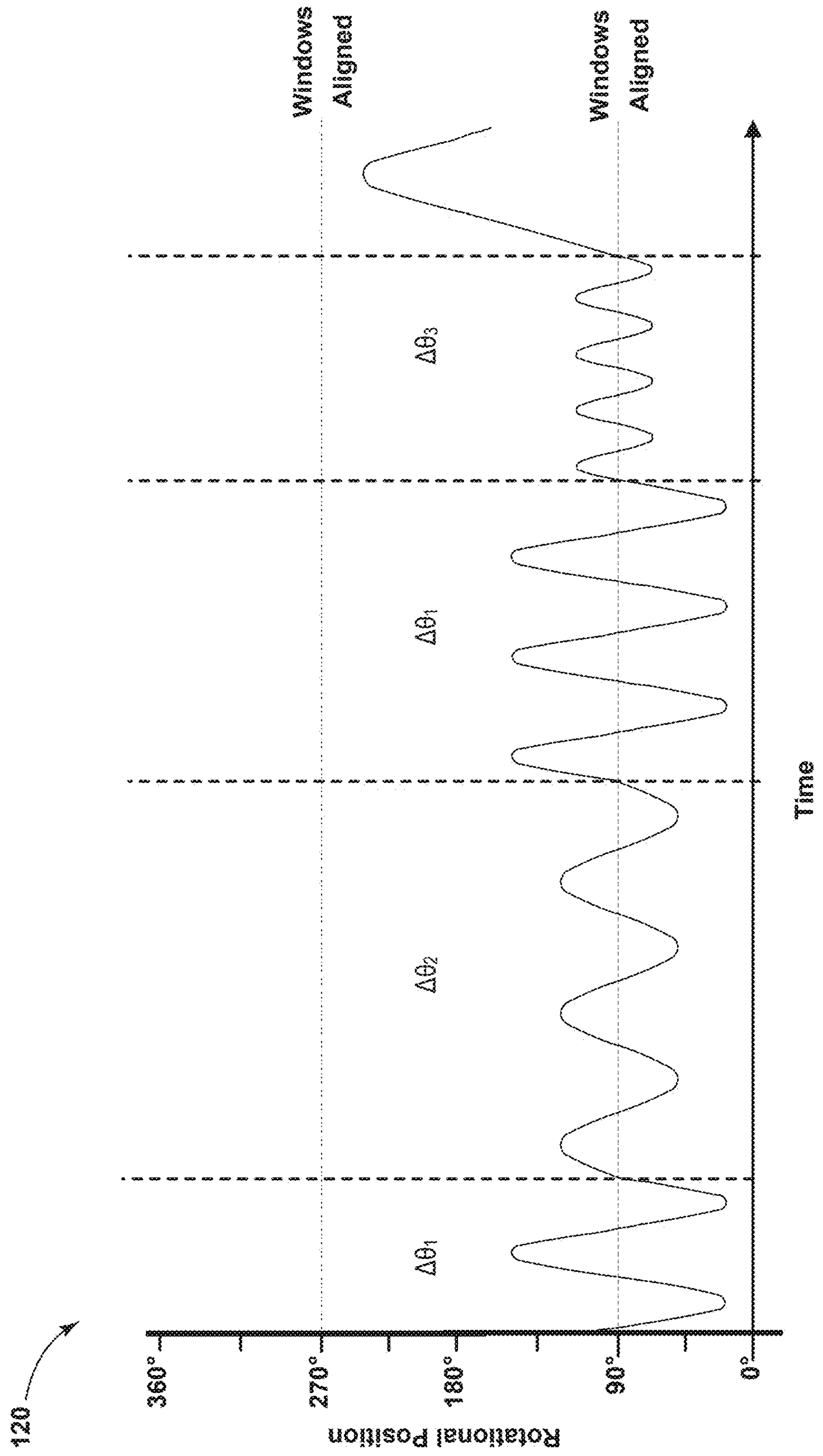
FIG. 11 is a plot demonstrating the operation of a rotary cutting tool over a plurality of rotational ranges configured to selectively maintain an alignment of a cutting window.
Figure 12:
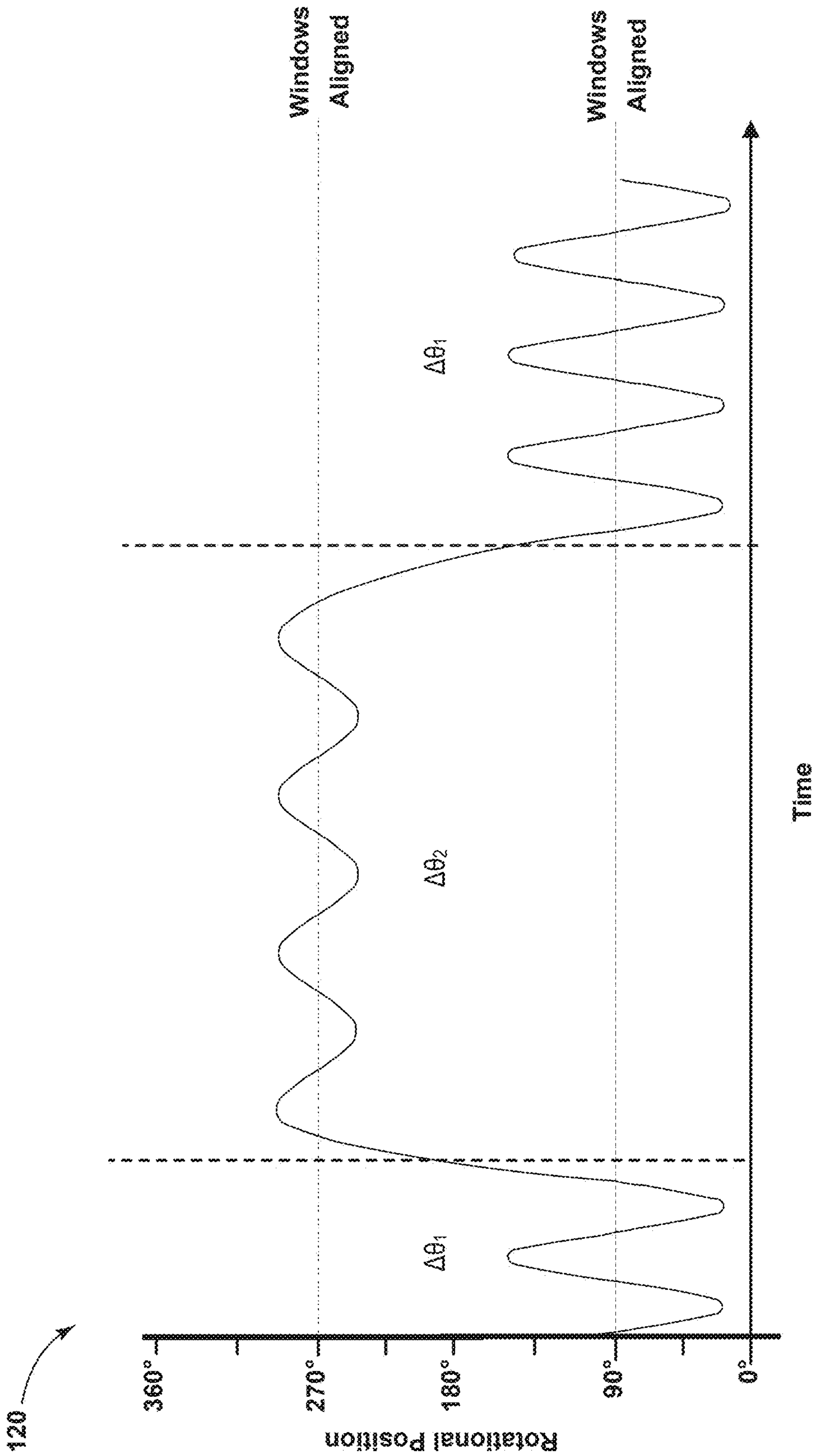
FIG. 12 is a plot demonstrating the operation of a rotary cutting tool over a plurality of rotational ranges configured to selectively maintain an alignment of a plurality of cutting windows.

Referring now to FIG. 11, the operation of the cutting apparatus 10 may be controlled over the various angular ranges (e.g., Δθ1, Δθ2, Δθ3) to adjust or vary the prioritization of maintaining the flow passage 130. In the example shown, the angular range 40 is controlled over a first angular range 401, a second angular range 402, and a third angular range Δθ3. In the example shown in FIG. 11, each of the angular ranges Δθ1, Δθ2, and Δθ3 are centered, such that the extremes of the rotational position θ are bisected or centered on the alignment of the windows 62, 64, thereby maximizing the opening of the flow passage 130 throughout operation. As shown, the range of the rotational position θ may be greater over the first angular range Δθ1 than the second angular range Δθ2. Further, the range of the rotational position θ over the third angular range 403 may be less than the second angular range Δθ2. Accordingly, the exemplary control routine demonstrated in FIG. 11 may include a plurality of different angular ranges 40 that may be arranged in various sequences to adjust the temporal alignment of the windows 62, 64 and the corresponding flow passage 130. In this way, the cutting apparatus 10 may be controlled to adjust or maintain the proportions of the flow passage 130 throughout the cutting routine. Though described in reference to the angular ranges Δθ1, Δθ2, ΔΘ3 specifically centered on the alignment of the windows 62, 64, the operation of the cutting apparatus 10 may additionally be controlled to incrementally position the windows 62, 64 to maximize the flow passage 130 as later discussed in reference to FIG. 13.

In some implementations, the angular ranges Δθ1, 402 may be centered or defined based on the alignment of multiple inner windows 62*a*, 62*b* with the outer window 64. Such operation may be particularly beneficial when the window angles Ω1, Ω2 associated with the inner windows 62*a*, 62*b* differ in proportions. For example, as previously discussed in reference to FIG. 5C, the first inner window 62*a* may have a smaller window angle Ω1 relative to the second window angle Ω2 of the second inner window 62*b*. When implemented with a control procedure as demonstrated in FIG. 12, the first angular range Δθ1 may provide for an increased range of the rotational position θ relative to the second angular range Δθ2. Additionally, the first angular range 401 may be centered with the first inner window 62*a* aligned with the outer window 64. The second angular range 402 may be centered with the second inner window 62*b* aligned with the outer window 64. Accordingly, the operation of the inner rotary member 50 may vary over angular ranges 401, 402 and corresponding changes in the proportions of the first window angle Ω1 of the first inner window 62*a* and the second window angle Ω2 of the second inner window 62*b*. In this way, the controller 42 may provide for the control and alignment of the flow passage 130 between the outer window 64 and each of the inner windows 62*a*, 62*b*, such that the angular ranges 401, 402 provide for controlling or maintaining the proportions of the flow passage 130 based on the desired operation of the cutting apparatus 10 and the window angles Ω1, Ω2 of the plurality of inner windows 62.

Figure 13:
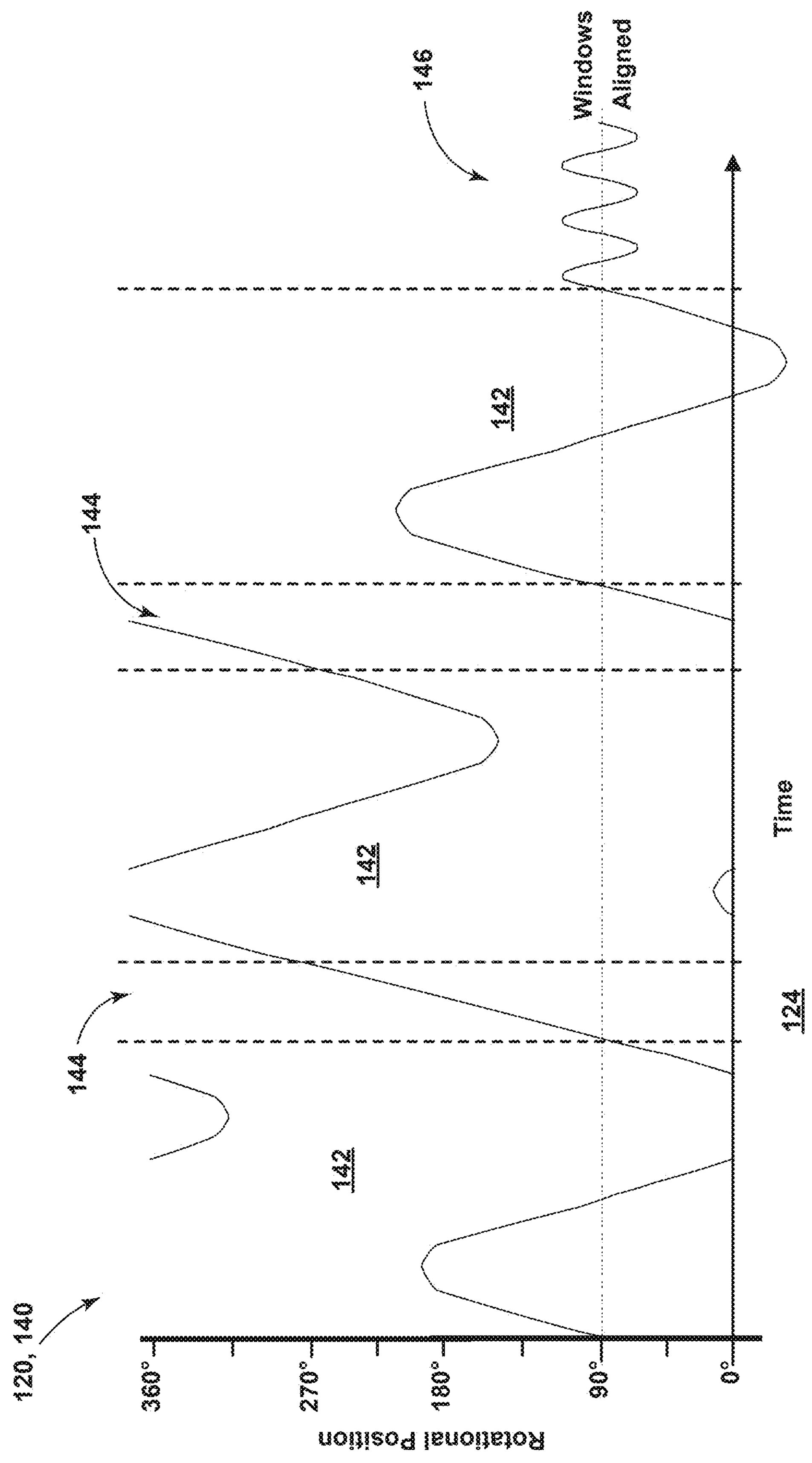
FIG. 13 is a plot demonstrating the operation of a rotary cutting tool over successive relative positions configured to control an alignment of a cutting window based on a cyclical alignment of an incremental or relative control of an angular position.

Referring now to FIG. 13, the alignment of the windows 62, 64 and corresponding maintenance of the flow passage 130 may be maintained by controlling the relative rotational position θ of the inner rotary member 50 over time. As demonstrated in the plot 120 of FIG. 13, a control routine 140 is shown demonstrating a plurality of oscillating segments 142 separated by intervening transition segments 144. In operation, the controller 42 may control the motor drive circuit 144 to adjust the rotational position θ over a like or similar number of clockwise and counterclockwise steps, intervals, or drive cycles in each of the oscillating segments 142. During the transition segments 144, the controller 42 may continue to control the rotational position θ to continue in either the clockwise or counterclockwise direction. In the example shown, the controller 42 continues to adjust the rotational position θ in the clockwise direction over an interval approximately equal to twice the amplitude of the change in the rotational position θ during the foregoing oscillating segment 142. In this way, the transition segments 144 may adjust the relative rotational position θ to extend over a different range of the rotational position θ in each successive oscillating segment 142.

In the example shown, approximately every other oscillating segment is centered with the angular range 40 centered on the flow passage 130 with the windows 62, 64 aligned. In this way, the controller 42 may adjust the rate of change of the rotational position θ and the relative rotational position θ in the alternating segments 142, 144 to ensure that the windows 62, 64 are aligned for a predetermined frequency and duration, thereby ensuring the flow passage 130 is opened sufficiently to remove fluid and debris from the patient's surgical cavity. Though the difference in the rotation angle in the example shown is approximately double in the clockwise or first direction, the rotational difference may be greater than 10%, 20%, 50%, 150%, 200% or more. In general, the difference in magnitude between the rotation in the first direction compared to the second direction may be controlled by the controller based on a duration and/or a rate of the rotary member in the first direction or the second direction.

As further demonstrated in FIG. 13, the relative control of the rotational position θ and corresponding segments 142, 144 of the control routine 140 may be implemented in combination with various other control routines. For example, following the alternating series of the oscillating segments 142 and the transition segments 144, the controller 42 may adjust the rotation of the inner rotary member 50 to return to a control structure where the rotational position θ varies over a balanced alternating sequence 146 or an angular range 40, similar to the control routines discussed in reference to FIGS. 8, 11, and 12. Though described as being controlled over a specific angular range 40, a balanced alternating sequence may be controlled based on a relative position of the motor 46/cutting member 50 by activating the motor 46 in alternating directions over intervals that are approximately equal or less the 10% or less than θ% different in directional magnitude or the resulting change in the rotational position θ.

As described in various examples, the controller 42 may be configured to operate with a variety of control schemes depending upon the features of the cutting apparatus 10, a procedure type, and/or a user preference. For example, based on the procedure type, one or more of the control routines or control methods for the cutting apparatus 10 may be pre-loaded or suggested via the user interface 16 of the control console 14. Similarly, the routines and/or control methods discussed herein may be activated or suggested for the operation of the cutting apparatus 10 in response to the identification of a user profile and a corresponding operating preference and/or the identification of the cutting head 32, which may be responsive to a model or serial number indicated by the RFID tag or identification circuit as previously discussed.

The operation described in reference to FIG. 13 and other related operations disclosed may ensure that an average rate or frequency of an alignment between the at least one inner window 62 and the outer window 64 is maintained or set based on the biased alternating sequence. In this way, the opening between the windows 62, 64 may be maintained over a plurality of cycles of the biased alternating sequence by controlling a relative rotational position θ of the rotary member 50. In some cases, the difference between the first interval (e.g., clockwise) and the second interval (e.g., counterclockwise) may be expressed as a ratio of each of the alternating rotation angles in the opposing directions. By adjusting the ratio of the intervals, the controller may adjust or maintain a frequency or rate of the alignment frequency between the inner window 62 and the outer window 64. In this way, the controller may ensure that an effective aspiration rate from a cavity is maintained through aligned windows 62, 64 without monitoring, or in some cases without having the capability to monitor, an absolute value of the rotational position θ of the rotary member 50. In other words, the biased alternating sequence may provide for a relative motion control procedure that maintains a target, programmed or assigned average alignment rate or frequency between the windows 62, 64 without positional feedback and only relying on the rotational position θ following each successive rotation in the first direction or the second direction through the control routine.

Figure 14:
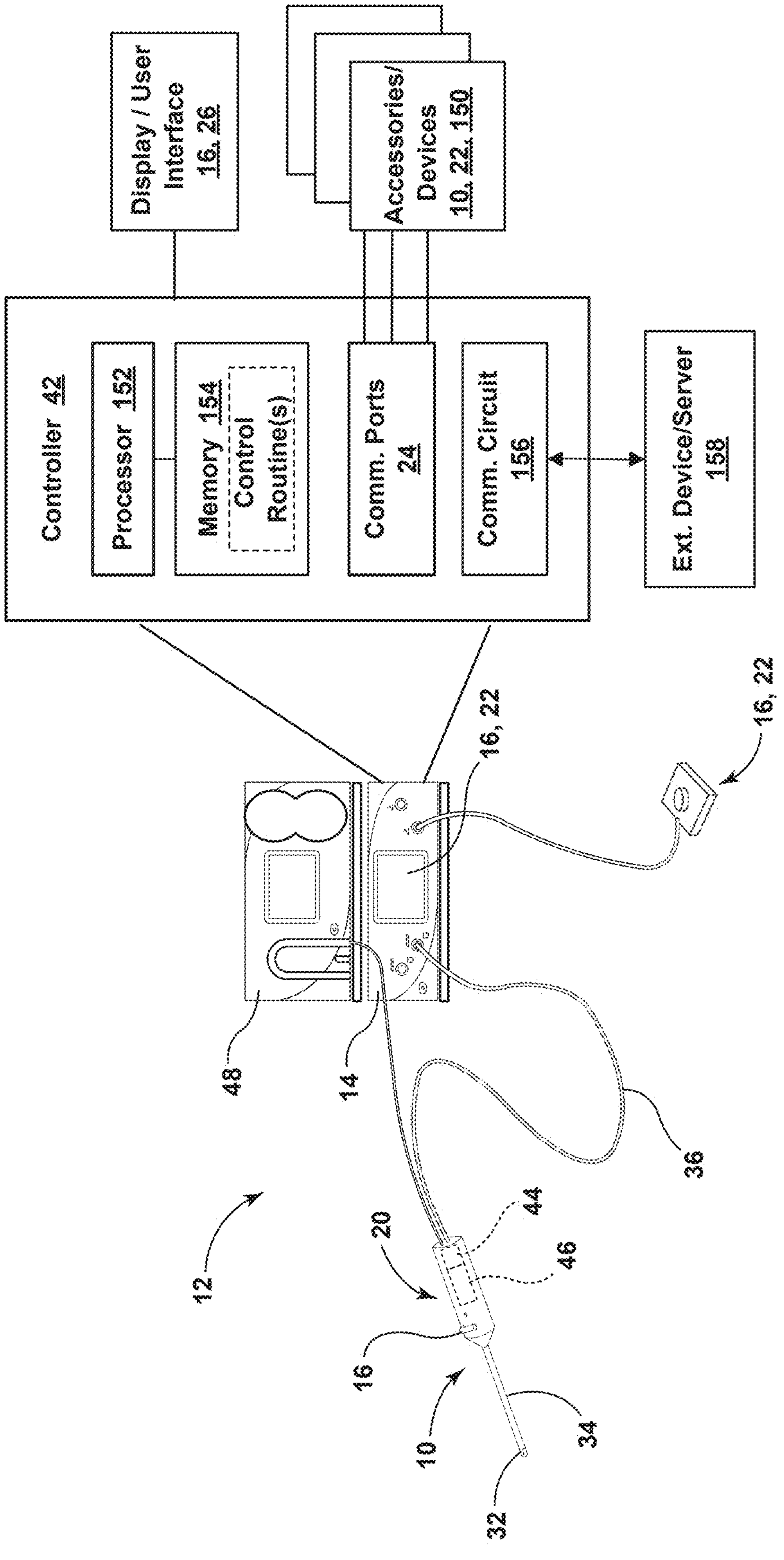
FIG. 14 is a pictorial block diagram demonstrating a surgical handpiece and control system for a control console in accordance with the disclosure.

Referring now to FIG. 14, the control system 12 is shown demonstrating the control console 14 and further details of the console controller 42. In operation, the controller 42 may receive inputs via one or more user interfaces 16 of the apparatus 10 and/or input accessories 22. In various examples, the operation of the system 12 is discussed in reference to the operation of the apparatus 10. However, it shall be understood that the operation of the system 12 may commonly provide for the concurrent use and control of two or more surgical devices 150, which may include various handpieces, peripheral devices, remote controls, and various other devices or accessories that may be beneficial in a medical or surgical environment. For example, the surgical devices 150 may include various laser or radio frequency cutting or operating utilities in the form of ablation devices, catheters, pumps, suction or aspiration devices, and similar tools that may be in communication with the control console 14 via the communication ports 24 or various other communication connection (e.g., a device network).

As discussed throughout the disclosure, the system 12 may provide for coordinated communication and control of the rotary surgical apparatus 10 in coordination with the operation of the pump 48. For example, a suction rate or intensity of the pump 48 may be controlled in coordination with one or more operating sequences and corresponding duty cycles of the cutting windows 40. Similarly, the operation of the pump 48 may be controlled in response to the rotational position θ or changes in the rotational position θ of the inner rotary member 50 over time. To effectuate the various operations of the cutting apparatus 10 and the coordinate operation of the pump 48, the controller 42 may communicate with and/or control the pump 48 over a device network exemplified by the communication port(s) 24. In this way the operation of the cutting apparatus 10 may be controlled in coordination with the operation of the pump 48.

Additionally, the controller 42 or the system 12 may determine or access information defining the model, style, dimensions, operating ranges, etc. for the cutting head 42. For example, the selective positioning and tracking of the alignment of the window 62, 64 and various features of the cutting heads 32 may be achieved by accessing information identifying the arrangement of the inner window(s) 62, the outer window 64, the window angles ω, and the rotational positions θ, and other information that may among the cutting heads 42. Such model or accessory information may be programmed into, accessed by, or otherwise identified by the controller 42 for each of the configurations of the cutting head 32. For example, the cutting style, features, and dimensions of the cutting windows 62, 64 may be identified in response to a manual programming input, selection in an accessory library or database, and/or detected by the controller 42 based on information accessed from the cutting head 32. In some cases, identifying style, model, dimensional, operating speed ranges and limits, usage restrictions (time limits, cutting pass limits, etc.), manufacturer information, usage statistics and various forms of information related to the cutting head 32 may be accessed by the controller 42. Such information may be accessed via an electronic identification circuit or tag (e.g., radio frequency identification [RFID]) incorporated in the cutting head 32 (e.g., the hub adapter 70). The electronic identification circuit may be accessed by the controller 42 by one or more communication circuits 156 or communication ports 24. In this way, the controller 42 may update the operation of the cutting apparatus 10 in response to the specific style, dimensions, and operating configurations of each of the interchangeable cutting heads 32.

In some implementations, the system 12 may include one or more display screens 26 that communicate with various controllers and surgical devices 150 similar to those discussed herein. In some examples, the system 12 may be in communication with one or more imaging devices, which may be connected to or in communication with the control console 14. The image data captured by such surgical devices 150 may be presented by one or more communicatively connected display devices (e.g., display monitors). In various implementations, the image data may be displayed in conjunction with one or more status notifications indicating the operating routine or sequence of cutting styles applied by console 14 to control the cutting apparatus 10. Additionally, operating instructions may be selectively displayed on one or more of the display screens 26 identifying or mapping the function of each input of one or more of the user interfaces 16 to the functions or cutting operations of the cutting apparatus 10. In this way, the active configuration (e.g., a 60/40 duty cycle between two-cutting windows 62*a*, 62*b*) may be identified in the status notification and adjustment instructions may be shown indicating how to adjust the active configuration to a different duty cycle or operating routine or sequence in accordance with the disclosure.

As previously discussed, the control console 14 may be in communication with one or more surgical devices 150 or accessories 22 that may be associated with the operation of the control console 14. For example, the accessories 22 may correspond to one or more electronic or electromechanical buttons, triggers or pedals (e.g., pressure sensitive or single actuation foot pedals), and additional devices communicatively connected to the communication ports 24. The display screen 26/user interface 16 of the control console 14 may include one or more switches, buttons, dials, and/or displays, which may include soft-key or touchscreen devices incorporated in a display (e.g., liquid crystal display [LCD], light emitting diode [LED] display, cathode ray tube [CRT], etc.). In response to inputs received from the display screen 26 and/or user interface 16, the controller 42 may activate or adjust the settings of the control signals communicated to the apparatus 10. The control signals generated by the console controller 42 may be configured for operation in response to the selected operating configuration, routine, duty cycle, etc. The output signals communicated from the communication port 24 to the surgical apparatus 10 may be generated by various signal generators, motor controllers, or power supplies that may provide for operation of power electronic operations (e.g., motor drive signals and supply current), which may be controlled and configured for operation based on the instructions, commands, or signals communicated from a processor 152 of the controller 42 for the associated operating configuration. Accordingly, the console controller 42 may be operable to generate signals to drive or control the motion, rotation, activation, intensity, and various other operating characteristics of the surgical apparatus 10.

The processor(s) 152 of the controller 42 may be implemented as one or more microprocessors, microcontrollers, application-specific integrated circuits (ASIC), or other circuitry configured to perform instructions, computations, and control various input/output signals to control the control system 12. The instructions and/or control routines of the system 12 may be accessed by the processor(s) 152 via a memory 154. The memory 154 may comprise random access memory (RAM), read only memory (ROM), flash memory, hard disk storage, solid state drive memory, etc. Each of the processors 152 and memory devices 154 may be implemented to suit the corresponding functionality or sophistication of the surgical apparatus 10 and the corresponding control requirements of the controller 42.

The controller 42 may incorporate additional communication circuits or input/output circuitry, generally represented in FIG. 10 as the communication circuit(s) 156, which may be implemented to communicate with one or more peripherals, devices, remote computers or servers 158, etc. The communication circuit(s) 156 may complement or support the operating capability of the communication ports 24. In general, the communication circuit 156 may provide for communication via a variety of communication protocols to support operation of the surgical apparatus 10. In an exemplary embodiment, the circuitry associated with the communication ports 24 may include digital-to-analog converters, analog-to-digital converters, digital inputs and outputs, as well as one or more communication interfaces or buses. The circuits associated with the communication ports 24 and/or the communication circuit 156 may be implemented with various communication protocols, such as serial communication (e.g., CAN bus, I2C, etc.), parallel communication, or network communication (e.g., RS232, RS485, Ethernet). In some cases, the communication circuit 156 may also provide for wireless network communication (Wi-Fi, Bluetooth®, Ultra-wideband [UWB], etc.). In some examples, the controller 42 may be in communication with one or more of the external devices 150 (e.g., control devices, peripherals, servers, etc.) via the communication circuit 156. Accordingly, the control console 14 may provide for communication with various devices to update, maintain, and control the operation of the system 12.

According to some aspects of the disclosure, a rotary surgical apparatus comprises an outer housing forming an interior passage extending from an engagement end portion to an acting end portion. The outer housing forms an opening along the acting end portion and a rotary member extends through the interior passage and in connection with a motor at a proximal end portion and forming at least one cutting window at a distal end portion, wherein the rotary member rotates within the interior passage selectively positioning the at least one cutting window relative to the opening. A controller in communication with the motor, wherein the controller is configured to control the motor to rotate the rotatory member in a biased alternating sequence between a first direction and a second direction opposite the first direction. The controller activates the motor to drive the rotary member in the first direction for a first interval and the second direction for a second interval. The first interval is greater than the second interval.

According to various aspects, the disclosure may implement one or more of the following features or configurations in various combinations:

- a frequency of an alignment between the at least one window and the opening is maintained over a plurality of cycles of the biased alternating sequence by controlling a relative rotational position of the rotary member;
- the controller controls a ratio of the first interval to the second interval, thereby controlling an alignment frequency between the cutting window and the opening;
- the frequency of the alignment is adjusted based on an aspiration setting of the rotary surgical apparatus;
- the biased alternating sequence is selectively activated alternatively with a balanced alternating sequence;
- the controller controls the motor to rotate the rotary member in approximately equal intervals in the first direction and the second direction in the balanced alternating sequence;
- the biased alternating sequence is activated in response to a user input to a user interface of the controller;
- the first interval rotates the rotary member over a first rotation angle and the second interval rotates the rotary member over a second rotation angle, wherein the first rotation angle is greater than the second rotation angle;
- the first rotational angle is at least 10% greater than the second rotation angle;
- the first rotational angle is at least 50% greater than the second rotation angle;

a rotation difference between the first rotation angle and the second rotation angle causes the window to align with the opening at a controlled frequency;

a rotational start position of the rotary member for each successive rotation in the first direction or the second direction is controlled relative to a rotation end position of a previous rotation;

the motor controls successive rotations of the alternating sequence based on a relative position control;

the controller an absolute rotational position of the rotary member is not monitored in controlling the motor in the biased alternating sequence;

the controller adjusts the rotational position in the first direction and second direction without regard adjusting an absolution rotational position of the rotary member or the motor; and/or the greater magnitude of the first interval relative to the second interval is controlled by the motor based on a duration or a rate of the rotary member in the first direction or the second direction.

According to another aspect of the disclosure, a method is provided for controlling an arthroscopic surgical tool including a rotary member with a cutting window that selectively aligns rotationally with an opening. The method comprises rotating the rotary member in a first direction over a first interval and rotating the rotary member in a second direction, opposite the first direction, over a second interval, wherein the first interval is greater than the second interval, and wherein a ratio of the first interval to the second interval controls an alignment frequency between the cutting window and the opening.

According to various aspects, the disclosure may implement one or more of the following features or configurations in various combinations:

the alignment frequency is adjusted based on an aspiration setting of the rotary surgical apparatus;

a rotational start position of the rotary member for each successive rotation in the first direction or the second direction is controlled relative to a rotation end position of a previous rotation; and/or the first interval rotates the rotary member over a first rotation angle and the second interval rotates the rotary member over a second rotation angle, wherein the first rotation angle is at least 10% greater than the second rotation angle.

According to yet another aspect of the disclosure, a rotary surgical apparatus comprises an outer housing forming an interior passage extending from an engagement end portion to an acting end portion, with the outer housing forming an opening along the acting end portion. A rotary member extends through the interior passage and in connection with a motor at a proximal end portion and forms at least one cutting window at a distal end portion. The rotary member rotates within the interior passage selectively positioning the at least one cutting window relative to the opening. A controller is in communication with the motor and configured to control the motor to position the rotary member over a first angular range overlapping the at least one window with the opening in a first cutting sequence; control the motor to position the rotary member over a second angular range; overlapping the at least one window with the opening in a second cutting sequence; and selectively adjust a duty cycle between the first cutting sequence and the second cutting sequence.

According to various aspects, the disclosure may implement one or more of the following features or configurations in various combinations:

the second angular range is less than the first angular range;

the second angular range maintains an at least partial alignment between the at least one cutting window and the opening over the corresponding rotation of the rotary member;

the duty cycle adjusts proportion of time of an alternating rotation between the first angular range and the second angular range;

the at least one cutting window comprises a plurality of cutting windows including a first window and a second window at the distal end portion;

the duty cycle adjusts a sequence of the alternating rotation to apply the first angular range over a first cutting percentage;

the first cutting percentage ranges from 5% to 95% and controls the first window to oscillate along the first angular range for the first cutting percentage;

the duty cycle adjusts a sequence of the alternating rotation to apply the second angular range over a second cutting percentage;

the second cutting percentage ranges from 5% to 95% and controls the second window to oscillate along the second angular range for the second cutting percentage;

the controller is further configured to control the motor to position the rotary member over a third angular range aligned with a portion of the first window and a portion of the second window defining a third cutting sequence;

the first window comprises a first cutting edge and a second cutting edge, and the second window comprises a third cutting edge and a fourth cutting edge, wherein the cutting edges comprise a plurality of cutting profiles, and wherein the cutting edges of the windows form pairs of opposing rotary cutting surfaces;

the plurality of cutting profiles comprise two or more of a serrated edge, a scalloped edge, a wavy edge, and a straight edge;

the first cutting edge and the second cutting edge have a first cutting profile;

the third cutting edge has second cutting profile different from the first cutting profile;

the opening formed by the outer housing comprises a plurality of fixed edges rotationally engaged by the plurality of cutting edges;

the plurality of fixed edges comprise a third cutting profile;

the controller is further in communication with a pump configured to adjust a fluid flow through the rotary surgical apparatus;

the controller is further configured to identify an alignment proportion between at least one of the cutting windows and the opening;

the controller is configured to communicate an indication of a pump setting adjustment to the pump in response to the alignment proportion; and/or the controller is further configured to communicate an indication of a pump setting to the pump responsive to at least one of a rotational position of the rotary member, an alignment of the cutting windows with the opening, and rotational or oscillating speed of the rotary member.

According to still another aspect of the disclosure, a method for controlling an arthroscopic surgical tool is provided. The method includes controlling a first oscillating rotation of a rotary member over a first angular range; controlling a second oscillating rotation of the rotary member over a second angular range different from the first angular range; activating a plurality of combined cycles of the first oscillating rotation over a first plurality of cycles to the second oscillating rotation over a second plurality of cycles; and controlling an activation ratio of the first plurality of cycles to the second plurality of cycles.

According to various aspects, the disclosure may implement one or more of the following features or configurations in various combinations:

- adjusting the activation ratio from the first plurality of cycles to a third plurality of cycles, and adjusting the activation ratio from the second plurality of cycles to a fourth plurality of cycles, thereby updating the activation ratio;
- the activation ratio is adjusted to control 20% to 80% of the combined cycles to be applied as the first oscillating rotation over the first angular range;
- the activation ratio is adjusted to control 20% to 80% of the combined cycles to be applied as the second oscillating rotation over the second angular range;
- the plurality of combined cycles comprises activations of the first oscillating motion for the first plurality of cycles alternated with the second oscillating motion for the second plurality of cycles;
- the first angular range is different than the second angular range;
- the first angular range includes an alignment of a first cutting edge of a first cutting window and a second cutting edge of the first cutting window of a rotary member with an opening in a housing through which the rotary member extends;
- the second angular range includes an alignment of a third cutting edge of a second cutting window and a fourth cutting edge of the second window of the rotary member with the opening in the housing; and/or
- the first angular range includes an alignment of a first cutting edge of a first cutting window and a second cutting edge of a second cutting window of a rotary member with an opening in a housing through which the rotary member extends.

According to another aspect of the disclosure, a rotary surgical shaver comprises an outer housing forming an outer cutting window at a distal end portion. A rotary member extends through the outer housing and in connection with a motor at a proximal end portion and forms a plurality of cutting windows including a first window and a second window at the distal end portion. A controller is configured to control the motor to position the rotary member over a first angular range aligned with the first window defining a first cutting sequence; control the motor to position the rotary member over a second angular range aligned with the second window defining a second cutting sequence; and selectively adjust a duty cycle between the first cutting sequence and the second cutting sequence.

According to various aspects, the disclosure may implement the following features or configurations in various combinations:

- the duty cycle controls a combined a portion of a combined operating sequence comprising alternating rotations of the first cutting sequence and the second cutting sequence.

It will be understood that any described processes or steps within described processes may be combined with other disclosed processes or steps to form structures within the scope of the present device. The exemplary structures and processes disclosed herein are for illustrative purposes and are not to be construed as limiting.

It is also to be understood that variations and modifications can be made on the aforementioned structures and methods without departing from the concepts of the present device, and further it is to be understood that such concepts are intended to be covered by the following claims unless these claims by their language expressly state otherwise.

The above description is considered that of the illustrated embodiments only. Modifications of the device will occur to those skilled in the art and to those who make or use the device. Therefore, it is understood that the embodiments shown in the drawings and described above are merely for illustrative purposes and not intended to limit the scope of the device, which is defined by the following claims as interpreted according to the principles of patent law, including the Doctrine of Equivalents.

The invention claimed is:

1. A rotary surgical apparatus comprising:

an outer housing forming an interior passage extending from an engagement end portion to an acting end portion, the outer housing forming an opening along the acting end portion;

a rotary member extending through the interior passage and in connection with a motor at a proximal end portion and forming at least one cutting window at a distal end portion, wherein the rotary member rotates within the interior passage selectively positioning the at least one cutting window relative to the opening; and a controller in communication with the motor, wherein the controller controls the motor to rotate the rotary member in a biased alternating sequence between a first direction and a second direction opposite the first direction, wherein the controller activates the motor to drive the rotary member in the first direction for a first interval and the second direction for a second interval, wherein the first interval is greater than the second interval.

2. The rotary surgical apparatus according to claim 1, wherein a frequency of an alignment between the at least one cutting window and the opening is maintained over a plurality of cycles of the biased alternating sequence by controlling a relative rotational position of the rotary member.

3. The rotary surgical apparatus according to claim 1, wherein the controller controls a ratio of the first interval to the second interval, thereby controlling an alignment frequency between the at least one cutting window and the opening.

4. The rotary surgical apparatus according to claim 3, wherein the alignment frequency is adjusted based on an aspiration setting of the rotary surgical apparatus.

5. The rotary surgical apparatus according to claim 1, wherein the biased alternating sequence is selectively activated alternatively with a balanced alternating sequence.

6. The rotary surgical apparatus according to claim 5, wherein the controller controls the motor to rotate the rotary member in approximately equal intervals in the first direction and the second direction in the balanced alternating sequence.

7. The rotary surgical apparatus according to claim 1, wherein the biased alternating sequence is activated in response to a user input to a user interface of the controller.

8. The rotary surgical apparatus according to claim 1, wherein during the first interval, the rotary member is configured to rotate over a first rotation angle and during the second interval, the rotary member is configured to rotate over a second rotation angle, wherein the first rotation angle is greater than the second rotation angle.

9. The rotary surgical apparatus according to claim 8, wherein the first rotation angle is at least 10% greater than the second rotation angle.

10. The rotary surgical apparatus according to claim 8, wherein the first rotation angle is at least 50% greater than the second rotation angle.

11. The rotary surgical apparatus according to claim 8, wherein a rotational difference between the first rotation angle and the second rotation angle causes the at least one cutting window to align with the opening at a controlled frequency.

12. The rotary surgical apparatus according to claim 1, wherein a rotational start position of the rotary member for each successive rotation in the first direction or the second direction is controlled relative to a rotational end position of a previous rotation.

13. The rotary surgical apparatus according to claim 1, wherein the motor controls successive rotations of the biased alternating sequence based on a relative position control.

14. The rotary surgical apparatus according to claim 1, wherein an absolute value of the rotational position of the rotary member is not monitored in the biased alternating sequence.

15. The rotary surgical apparatus according to claim 1, wherein the controller adjusts the rotational position in the first direction and the second direction without monitoring an absolute value of the rotational position of the rotary member.

16. A method for controlling an arthroscopic surgical tool, the arthroscopic surgical tool comprising an outer housing forming an opening along an acting end portion thereof, a rotary member in connection with a motor at a proximal end portion thereof and comprising a cutting window that selectively aligns rotationally with the opening, and a controller which controls the motor to rotate the rotary member in a biased alternating sequence, the method comprising:

rotating the rotary member in a first direction over a first interval; and rotating the rotary member in a second direction, opposite the first direction, over a second interval, wherein the first interval is greater than the second interval, and wherein a ratio of the first interval to the second interval controls an alignment frequency between the cutting window and the opening.

17. The method according to claim 16, wherein the alignment frequency is adjusted based on an aspiration setting of the rotary surgical apparatus.

18. The method according to claim 16, wherein a rotational start position of the rotary member for each successive rotation in the first direction or the second direction is controlled relative to a rotational end position of a previous rotation.

19. The method according to claim 16, wherein during the first interval, the rotary member rotates over a first rotation angle and during the second interval, the rotary member rotates over a second rotation angle, wherein the first rotation angle is at least 10% greater than the second rotation angle.

20. A rotary surgical apparatus comprising:

an outer housing forming an interior passage extending from an engagement end portion to an acting end portion, the outer housing forming an opening along the acting end portion;

a rotary member extending through the interior passage and in connection with a motor at a proximal end portion and forming at least one cutting window at a distal end portion, wherein the rotary member rotates within the interior passage selectively positioning the at least one cutting window relative to the opening; and a controller in communication with the motor, wherein the controller:

controls the motor to position the rotary member over a first angular range overlapping the at least one cutting window with the opening in a first cutting sequence;

controls the motor to position the rotary member over a second angular range overlapping the at least one cutting window with the opening in a second cutting sequence; and selectively adjusts a duty cycle between the first cutting sequence and the second cutting sequence, wherein the second cutting sequence is a biased alternating sequence.

* * * * *